(12) United States Patent
Huang et al.

(10) Patent No.: US 9,477,082 B2
(45) Date of Patent: Oct. 25, 2016

(54) ANGULAR DISPLACEMENT DETECTING METHOD FOR ADAPTIVE OPTICS SYSTEM, IMAGING MAGNIFICATION DETECTING METHOD FOR ADAPTIVE OPTICS SYSTEM, AND ADAPTIVE OPTICS SYSTEM

(71) Applicant: HAMAMATSU PHOTONICS K.K., Hamamatsu-shi, Shizuoka (JP)

(72) Inventors: Hongxin Huang, Hamamatsu (JP); Takashi Inoue, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/895,517

(22) PCT Filed: May 29, 2014

(86) PCT No.: PCT/JP2014/064293
§ 371 (c)(1),
(2) Date: Dec. 3, 2015

(87) PCT Pub. No.: WO2014/196447
PCT Pub. Date: Dec. 11, 2014

(65) Prior Publication Data
US 2016/0109700 A1 Apr. 21, 2016

(30) Foreign Application Priority Data

Jun. 6, 2013 (JP) ................................. 2013-119851

(51) Int. Cl.
*G02F 1/01* (2006.01)
*G02F 1/03* (2006.01)
(Continued)

(52) U.S. Cl.
CPC ......... *G02B 27/0068* (2013.01); *A61B 3/1015* (2013.01); *A61B 3/12* (2013.01);
(Continued)

(58) Field of Classification Search
USPC ....... 359/239, 240, 559–564, 276, 278, 279, 359/245
See application file for complete search history.

(56) References Cited

U.S. PATENT DOCUMENTS 6,911,637 B1 * 6/2005 Vorontsov ............. G02B 26/06
250/201.9

FOREIGN PATENT DOCUMENTS

WO WO-2013/183341 A1 12/2013

OTHER PUBLICATIONS

Abdul Awwal, et al., "Characterization and Operation of a Liquid Crystal Adaptive Optics Phoropter," Proceedings of SPIE vol. 5169, 2003, pp. 104-122, December.
(Continued)

*Primary Examiner* — Mohammed Hasan
(74) *Attorney, Agent, or Firm* — Drinker Biddle & Reath LLP

(57) ABSTRACT

An adaptive optics system includes a spatial light modulator configured to spatially modulate a phase of an optical image incident on a modulation surface and a wavefront sensor including a lens array having a plurality of two-dimensionally arranged lenses and an optical detection element for detecting a light intensity distribution including converging spots formed by the lens array and configured to receive the optical image after the modulation from the spatial light modulator, and compensates for wavefront distribution by controlling a phase pattern displayed in the spatial light modulator based on a wavefront shape of the optical image obtained from the light intensity distribution, wherein an amount of angular displacement between the modulation surface and the wavefront sensor is calculated.

16 Claims, 39 Drawing Sheets

(51) Int. Cl.
*G02B 27/00* (2006.01)
*G01J 9/00* (2006.01)
*G01M 11/00* (2006.01)
*A61B 3/10* (2006.01)
*A61B 3/12* (2006.01)
*G01J 1/44* (2006.01)
*G01M 11/02* (2006.01)
*G02B 27/09* (2006.01)
*G02B 3/00* (2006.01)

(52) U.S. Cl.
CPC . *G01J 1/44* (2013.01); *G01J 9/00* (2013.01); *G01M 11/00* (2013.01); *G01M 11/02* (2013.01); *G02B 27/0927* (2013.01); *G02B 3/0006* (2013.01); *G02F 2203/12* (2013.01); *G02F 2203/18* (2013.01)

(56) References Cited

OTHER PUBLICATIONS

Chenxi Huang, et al., "Correlation matching method for high-precision position detection of optical vortex using Shack-Hartmann wavefront sensor," Optics Express vol. 20, No. 24, Nov. 2012, pp. 26099-26109, December.

Jason Porter, et al., "Adaptive Optics for Vision Science," Wiley Interscience, Chapter 18, 2006, pp. 496-499, December.

International Preliminary Report on Patentability dated Dec. 17, 2015 for PCT/JP2014/064293.

* cited by examiner

Fig.10
(a)
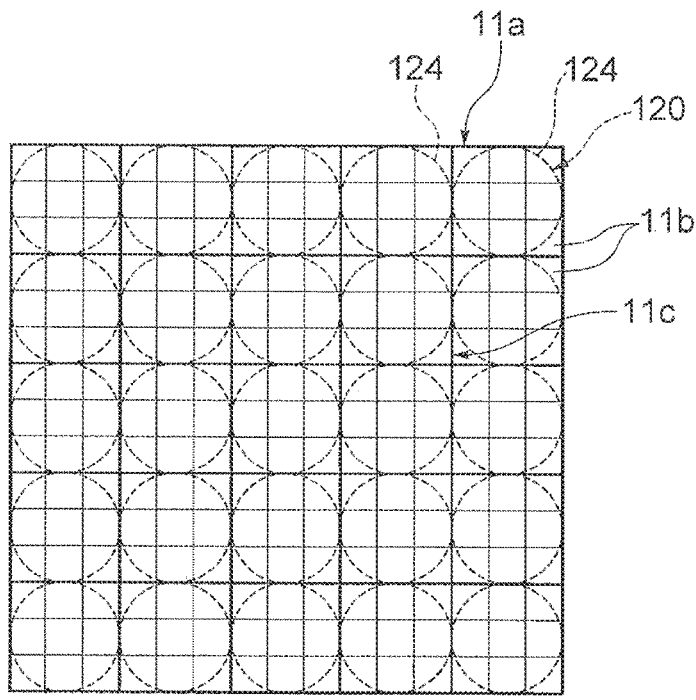
(b)
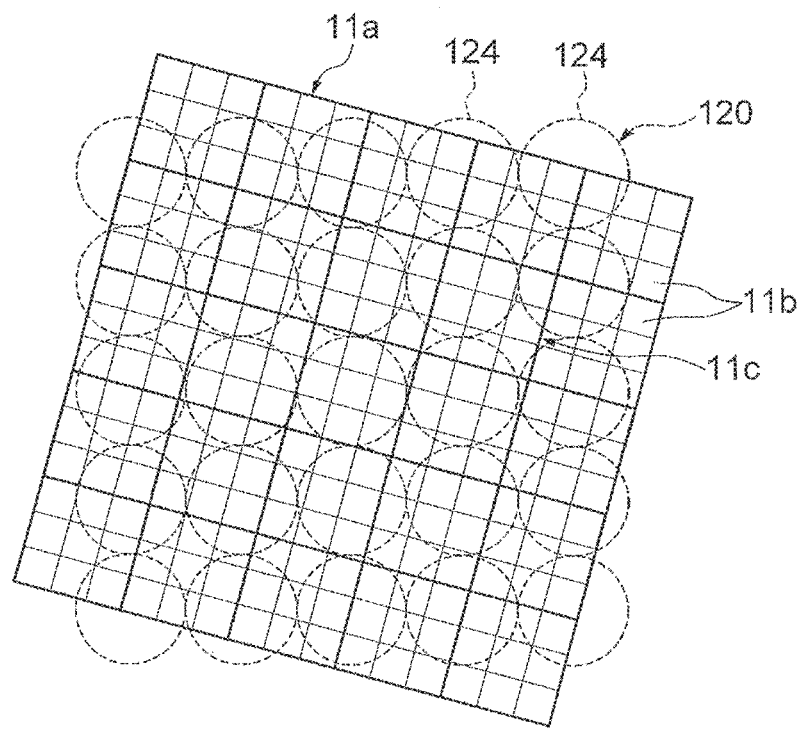

Fig.31
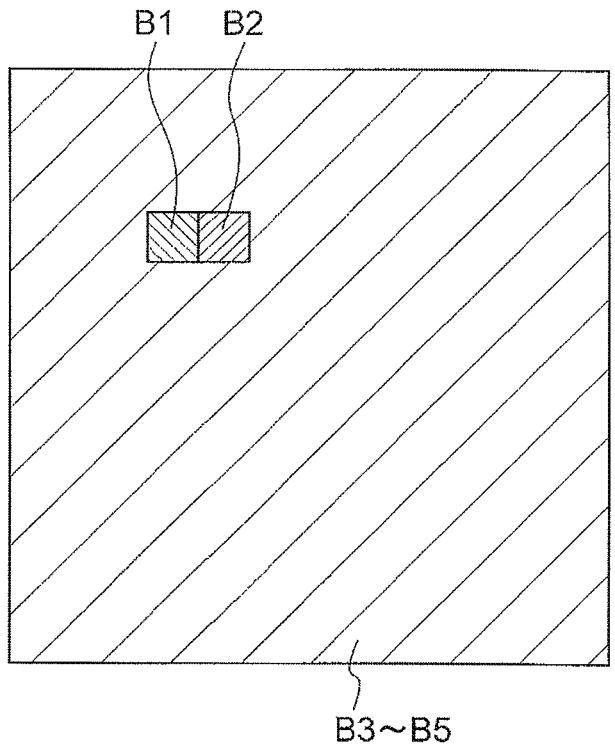
(a)
B3~B5
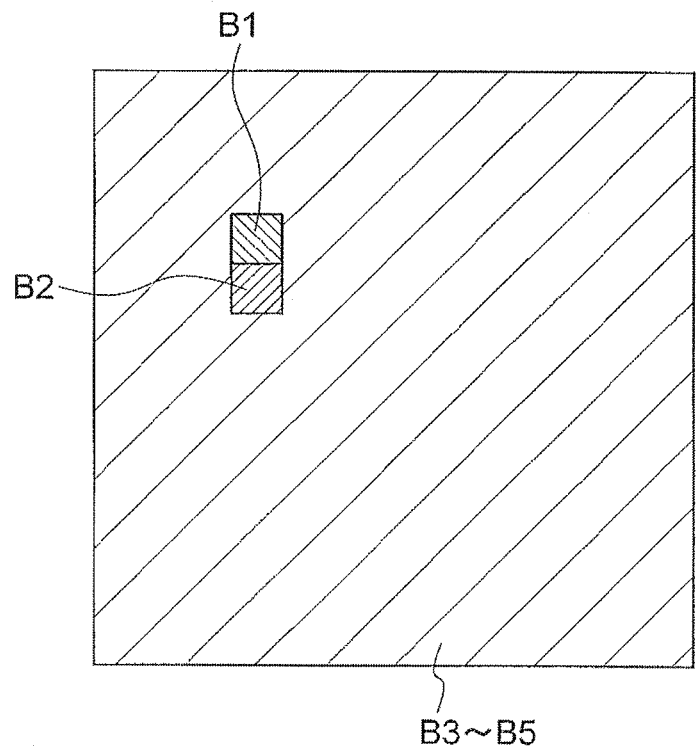
(b)
B3~B5

Fig.37
(a)
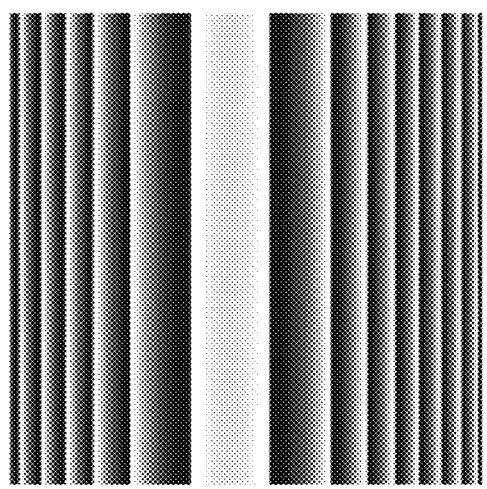
(b)
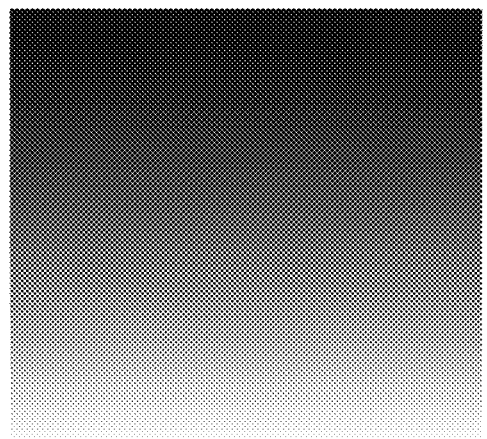
(c)
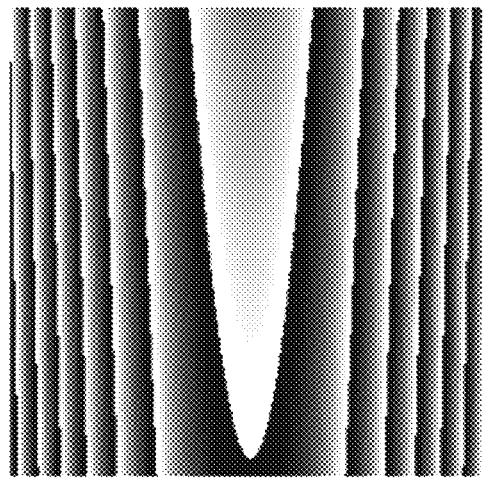

ANGULAR DISPLACEMENT DETECTING METHOD FOR ADAPTIVE OPTICS SYSTEM, IMAGING MAGNIFICATION DETECTING METHOD FOR ADAPTIVE OPTICS SYSTEM, AND ADAPTIVE OPTICS SYSTEM

TECHNICAL FIELD

An aspect of the present invention relates to an angular displacement detecting method for an adaptive optics system, an imaging magnification detecting method for an adaptive optics system, and an adaptive optics system.

BACKGROUND ART

In Non Patent Literatures 1 and 2, methods of adjusting an adaptive optics system according to a phase measuring method are disclosed. The phase measuring method is a method of measuring a phase distribution through a wavefront sensor after causing a spatial light modulator to display a known phase distribution and mutually associating coordinates on a modulation surface and coordinates on a detection surface by comparing a measurement result with the known phase distribution.

CITATION LIST

Non Patent Literature

[Non Patent Literature 1] Abdul Awwal, et al., "Characterization and Operation of a Liquid Crystal Adaptive Optics Phoropter," Proceedings of SPIE, Volume 5169, pp. 104-122 (2003)

[Non Patent Literature 2] Jason Porter, Hope Queener, Julianna Lin, Karen Thorn, and Abdul Awwal, "Adaptive Optics for Vision Science," Wiley Interscience, Chapter 18, pp. 496-499 (2006)

SUMMARY OF INVENTION

Technical Problem

Adaptive optics technology is technology for dynamically removing an aberration by measuring an optical aberration (wavefront distortion) using a wavefront sensor and controlling a wavefront modulation element (spatial light modulator) based on a measurement result. It is possible to improve an imaging characteristic, a degree of convergence, an SN ratio of an image, and measurement precision through the above-described adaptive optics technology. Conventionally, the adaptive optics technology was mainly used in astronomical telescopes and large laser apparatus. In recent years, the adaptive optics technology has been applied to ocular fundus cameras, scanning laser ophthalmoscopes, optical coherence tomography apparatus, laser microscopes, etc. Imaging using such adaptive optics technology enables observation at high resolution that was previously unavailable. For example, the ocular aberration is removed by applying the adaptive optics technology to an ocular fundus imaging apparatus for observing the back (ocular fundus) of the eye. For example, it is possible to clearly draw a microstructure of the ocular fundus such as a visual cell, a nerve fiber, or a capillary. The adaptive optics technology can be applied to the early diagnosis of diseases concerning circulatory system as well as ocular diseases.

In the adaptive optics system, a wavefront is controlled with precision of a light wavelength or less (for example, a sub-micro level). Therefore, angular displacement about an optical axis or a change in imaging magnification may occur between a modulation surface of a spatial light modulator and a wavefront sensor due to assembly precision of the wavefront sensor or the spatial light modulator, manufacturing errors of optical components and components for fixing the optical component, etc. When the angular displacement or the change in the imaging magnification is caused, a correspondence relation between a position of a control point in the spatial light modulator and a position of a measurement point in the wavefront sensor becomes incorrect and affects the precision of adaptive optics. Accordingly, it is desirable to easily detect the angular displacement and the imaging magnification between the modulation surface and the wavefront sensor in order to adjust a relative angle and imaging magnification between the modulation surface and the wavefront sensor. Also, for example, even when optical magnification between the modulation surface of the spatial light modulator and the wavefront sensor is variable, it is desirable to easily detect the imaging magnification between the modulation surface and the wavefront sensor.

An objective of an aspect of the present invention is to provide an angular displacement detecting method for an adaptive optics system and an adaptive optics system capable of easily detecting angular displacement about an optical axis between a modulation surface of a spatial light modulator and a wavefront sensor. Also, an objective of an aspect of the present invention is to provide an imaging magnification detecting method for an adaptive optics system and an adaptive optics system capable of easily detecting imaging magnification between a modulation surface of a spatial light modulator and a wavefront sensor.

Solution to Problem

An angular displacement detecting method for an adaptive optics system according to an aspect of the present invention is a method of calculating an amount of angular displacement between a modulation surface and a wavefront sensor in the adaptive optics system which includes a spatial light modulator configured to spatially modulate a phase of an optical image incident on the modulation surface and the wavefront sensor including a lens array having a plurality of two-dimensionally arranged lenses and an optical detection element for detecting a light intensity distribution including converging spots formed by the lens array and configured to receive the optical image after the modulation from the spatial light modulator and which compensates for wavefront distortion by controlling a phase pattern displayed in the spatial light modulator based on a wavefront shape of the optical image obtained from the light intensity distribution.

A first angular displacement detecting method includes a light intensity distribution acquiring step of acquiring the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions; and an angle calculating step of obtaining the amount of angular displacement between the modulation surface and the wavefront sensor based on a slope of a straight line connecting the converging spot corresponding to the first region and the converging spot corresponding to the second region included in the light intensity distribution obtained in the light intensity distribution acquiring step.

Also, a second angular displacement detecting method includes a first light intensity distribution acquiring step of acquiring a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region; a second light intensity distribution acquiring step of acquiring a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region; and an angle calculating step of obtaining the amount of angular displacement between the modulation surface and the wavefront sensor based on a slope of a straight line connecting the converging spot corresponding to the first region included in the first light intensity distribution and the converging spot corresponding to the second region included in the second light intensity distribution.

The first and second angular displacement detecting methods may further include: an adjusting step of adjusting an angle around the optical image of at least one of the modulation surface and the wavefront sensor so that the amount of angular displacement calculated in the angle calculating step is reduced.

Also, in the first and second angular displacement detecting methods, the first and second regions may be regions adjacent to each other or the first and second regions may be regions separated from each other.

An imaging magnification detecting method for an adaptive optics system according to an aspect of the present invention is a method of calculating imaging magnification between a modulation surface and a wavefront sensor in the adaptive optics system which includes a spatial light modulator configured to spatially modulate a phase of an optical image incident on the modulation surface and the wavefront sensor including a lens array having a plurality of two-dimensionally arranged lenses and an optical detection element for detecting a light intensity distribution including converging spots formed by the lens array and configured to receive the optical image after the modulation from the spatial light modulator and which compensates for wavefront distortion by controlling a phase pattern displayed in the spatial light modulator based on a wavefront shape of the optical image obtained from the light intensity distribution.

A first imaging magnification detecting method includes a light intensity distribution acquiring step of acquiring the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions; and a magnification calculating step of obtaining the imaging magnification between the modulation surface and the wavefront sensor based on a distance between the converging spot corresponding to the first region and the converging spot corresponding to the second region included in the light intensity distribution obtained in the light intensity distribution acquiring step.

Also, a second imaging magnification detecting method includes a first light intensity distribution acquiring step of acquiring a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region; a second light intensity distribution acquiring step of acquiring a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region; and a magnification calculating step of obtaining the imaging magnification between the modulation surface and the wavefront sensor based on a distance between the converging spot corresponding to the first region included in the first light intensity distribution and the converging spot corresponding to the second region included in the second light intensity distribution.

The first and second imaging magnification detecting methods may further include an adjusting step of adjusting the magnification of a light guide optical system arranged between the modulation surface and the wavefront sensor so that the imaging magnification calculated in the magnification calculating step is close to predetermined imaging magnification.

Also, the first and second imaging magnification detecting methods may further include an adjusting step of adjusting an optical distance between the modulation surface and the wavefront sensor so that the imaging magnification calculated in the magnification calculating step is close to predetermined imaging magnification.

Also, the first and second imaging magnification detecting methods may further include an adjusting step of adjusting a size of a region on the modulation surface in which the phase pattern for compensating for the wavefront distortion is displayed based on the imaging magnification calculated in the magnification calculating step.

Also, in the first and second imaging magnification detecting methods, the first and second regions may be regions adjacent to each other or the first and second regions may be regions separated from each other.

Also, an adaptive optics system according to an aspect of the present invention includes: a spatial light modulator configured to spatially modulate a phase of an optical image incident on a modulation surface; a wavefront sensor including a lens array having a plurality of two-dimensionally arranged lenses and an optical detection element for detecting a light intensity distribution including converging spots formed by the lens array and configured to receive the optical image after the modulation from the spatial light modulator; and a control unit configured to compensate for wavefront distortion by controlling a phase pattern displayed in the spatial light modulator based on a wavefront shape of the optical image obtained from the light intensity distribution.

In a first adaptive optics system, the control unit acquires the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions and obtains the amount of angular displacement between the modulation surface and the wavefront sensor based on a slope of a straight line connecting the converging spot corresponding to the first region and the converging spot corresponding to the second region included in the light intensity distribution.

Also, in a second adaptive optics system, the control unit acquires a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region, acquires a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region, and obtains the amount of angular displacement between the modulation surface and the wavefront sensor based on a slope of a straight line connecting the converging spot corresponding to the first region included in the first light intensity distribution and the converging spot corresponding to the second region included in the second light intensity distribution.

Also, in a third adaptive optics system, the control unit acquires the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions, and obtains the imaging magnification between the modulation surface and the wavefront sensor based on a distance between the converging spot corresponding to the first region and the converging spot corresponding to the second region included in the light intensity distribution.

Also, in a fourth adaptive optics system, the control unit acquires a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region, acquires a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region, and obtains the imaging magnification between the modulation surface and the wavefront sensor based on a distance between the converging spot corresponding to the first region included in the first light intensity distribution and the converging spot corresponding to the second region included in the second light intensity distribution.

Advantageous Effects of Invention

According to an angular displacement detecting method for an adaptive optics system and an adaptive optics system according to an aspect of the present invention, it is possible to easily detect angular displacement about an optical axis between a modulation surface of a spatial light modulator and a wavefront sensor. Also, according to an imaging magnification detecting method for an adaptive optics system and an adaptive optics system according to an aspect of the present invention, it is possible to easily detect imaging magnification between a modulation surface of a spatial light modulator and a wavefront sensor.

BRIEF DESCRIPTION OF DRAWINGS

FIG. 10 is a diagram conceptually illustrating a relative relation between the modulation surface and the lens array.

FIG. 25($b$) is a diagram illustrating light intensity distribution data in the case illustrated in FIG. 25($a$).

FIG. 26($b$) is a diagram illustrating light intensity distribution data in the case illustrated in FIG. 26($a$).

FIG. 27($b$) is a diagram illustrating light intensity distribution data in the case illustrated in FIG. 27($a$).

FIG. 31 is a diagram illustrating an example of an arrangement of first and second regions.

FIG. 37 is a diagram illustrating an example of a composite pattern obtained by superimposition.

DESCRIPTION OF EMBODIMENTS

Hereinafter, embodiments of an angular displacement detecting method for an adaptive optics system, an imaging magnification detecting method for an adaptive optics system, and an adaptive optics system according to an aspect of the present invention will be described with reference to the accompanying drawings. Also, the same elements are assigned the same reference signs in the description of the drawings and redundant description thereof will be omitted. Also, in the following description, it is assumed that a "phase distribution" indicates two-dimensionally distributed phase values, a "phase pattern" indicates a pattern obtained by coding the phase distribution (two-dimensional phase values) based on a certain standard, and a "phase profile" indicates a distribution of phase values in a certain direction (line) in the phase distribution.

(First Embodiment)

Figure 1:
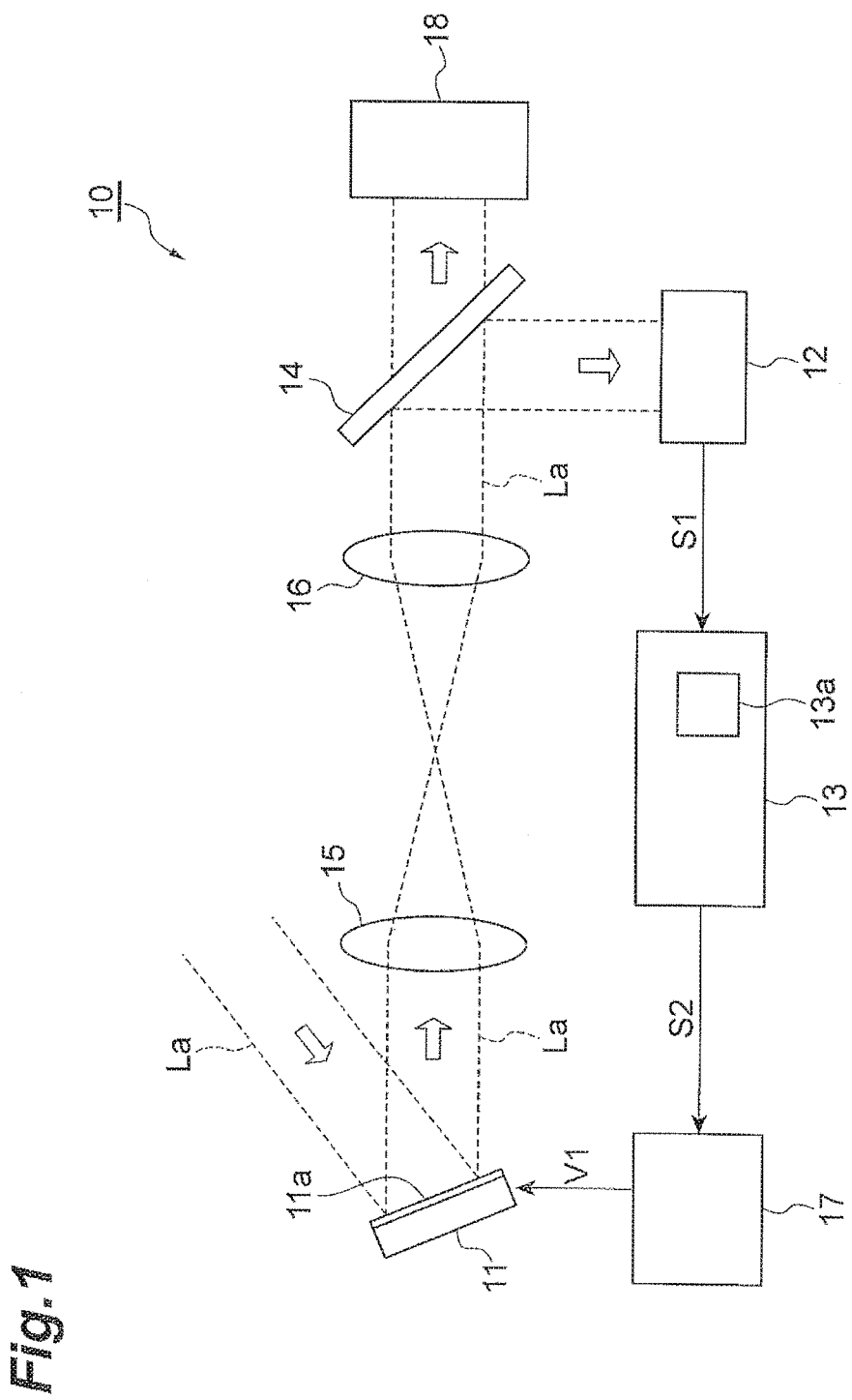
FIG. 1 is a diagram schematically illustrating a configuration of an adaptive optics system according to an embodiment.

FIG. 1 is a diagram schematically illustrating a configuration of an adaptive optics system 10 according to this embodiment. The adaptive optics system 10, for example, is embedded in an ophthalmologic inspection apparatus, a laser processing apparatus, a microscope apparatus, an adaptive optics apparatus, or the like. This adaptive optics system 10 includes a spatial light modulator (SLM) 11, a wavefront sensor 12, a control unit 13, a beam splitter 14, relay lenses 15 and 16, and a control circuit unit 17.

The spatial light modulator 11 receives an optical image La by a modulation surface 11a which displays a phase pattern and modulates a wavefront shape of the optical image La to output the modulated wavefront shape. The optical image La incident on the spatial light modulator 11, for example, is light emitted from a laser light source or a super luminescent diode (SLD) or reflected light, scattered light, fluorescent light, or the like generated from an observation object irradiated with light. The wavefront sensor 12 provides the control unit 13 with data S1 including information about the wavefront shape of the optical image La reaching from the spatial light modulator 11 (typically indicating distortion of a wavefront, that is, displacement of a wavefront from a reference wavefront, shown due to an aberration of an optical system). The control unit 13 generates a control signal S2 for displaying a phase pattern suitable for the spatial light modulator 11 based on the data S1 obtained from the wavefront sensor 12. In an example, the control unit 13 includes an input unit configured to input the data S1 from the wavefront sensor 12, an aberration calculation unit configured to calculate an aberration from the data S1, a phase pattern calculation unit configured to calculate a phase pattern to be displayed in the spatial light modulator 11, and a signal generation unit configured to generate the control signal S2 according to the calculated phase pattern. The control circuit unit 17 receives the control signal S2 from the control unit 13 and applies a voltage V1 based on the control signal S2 to a plurality of electrodes of the spatial light modulator 11.

The beam splitter 14 is arranged between the wavefront sensor 12 and the spatial light modulator 11 and branches the optical image La. The beam splitter 14 may be a beam splitter of a polarization direction independent type, a polarization direction dependent type, or a wavelength dependent type (dichroic mirror). One optical image La branched by the beam splitter 14, for example, is sent to an optical detection element 18 such as a CCD, a photomultiplier tube, or an avalanche photodiode. The optical detection element 18, for example, is embedded in a scanning laser ophthalmoscope (SLO), an optical coherence tomography (OCT) camera, an ocular fundus camera, a microscope, a telescope, or the like. In addition, the other optical image La branched by the beam splitter 14 is incident on the wavefront sensor 12.

The relay lenses 15 and 16 are arranged side by side in an optical axis direction between the spatial light modulator 11 and the wavefront sensor 12. The spatial light modulator 11 and the wavefront sensor 12 are maintained in a mutually optical conjugate relation by the relay lenses 15 and 16. Also, an optical imaging lens and/or a polarization mirror, etc. may be further arranged between the spatial light modulator 11 and the wavefront sensor 12.

Figure 2:
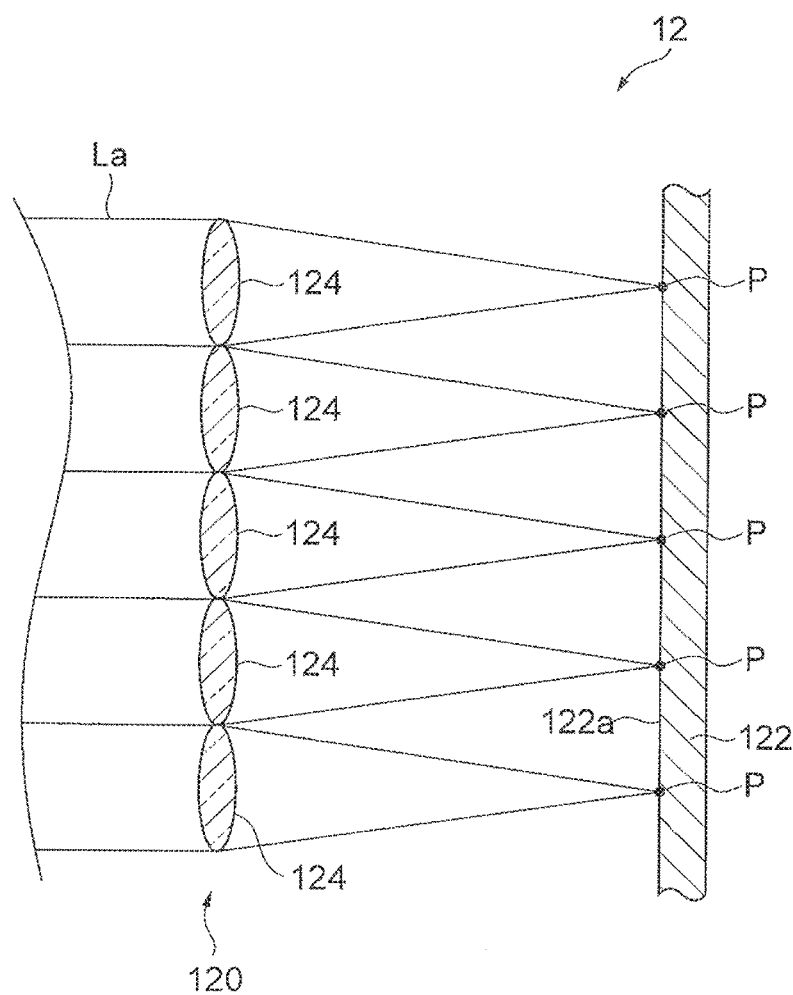
FIG. 2 is a cross-sectional view schematically illustrating a configuration of a wavefront sensor of an embodiment and illustrates a cross section along an optical axis of an optical image.
Figure 3:
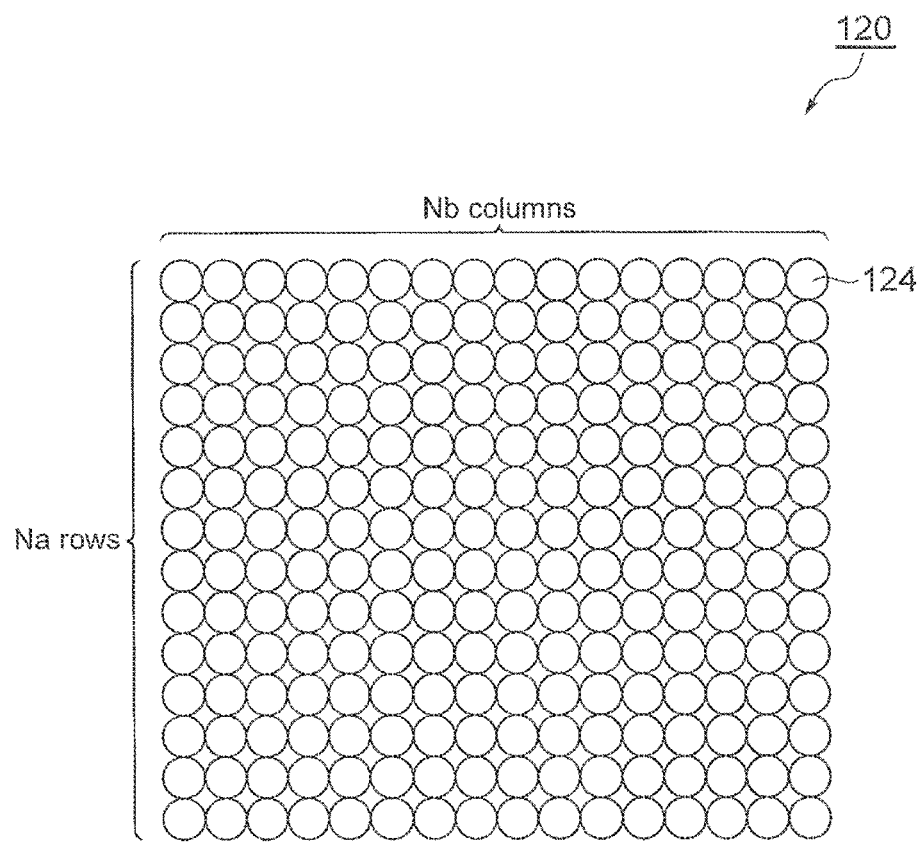
FIG. 3 is a view of a lens array provided in the wavefront sensor viewed in an optical axis direction of an optical image.
Figure 4:
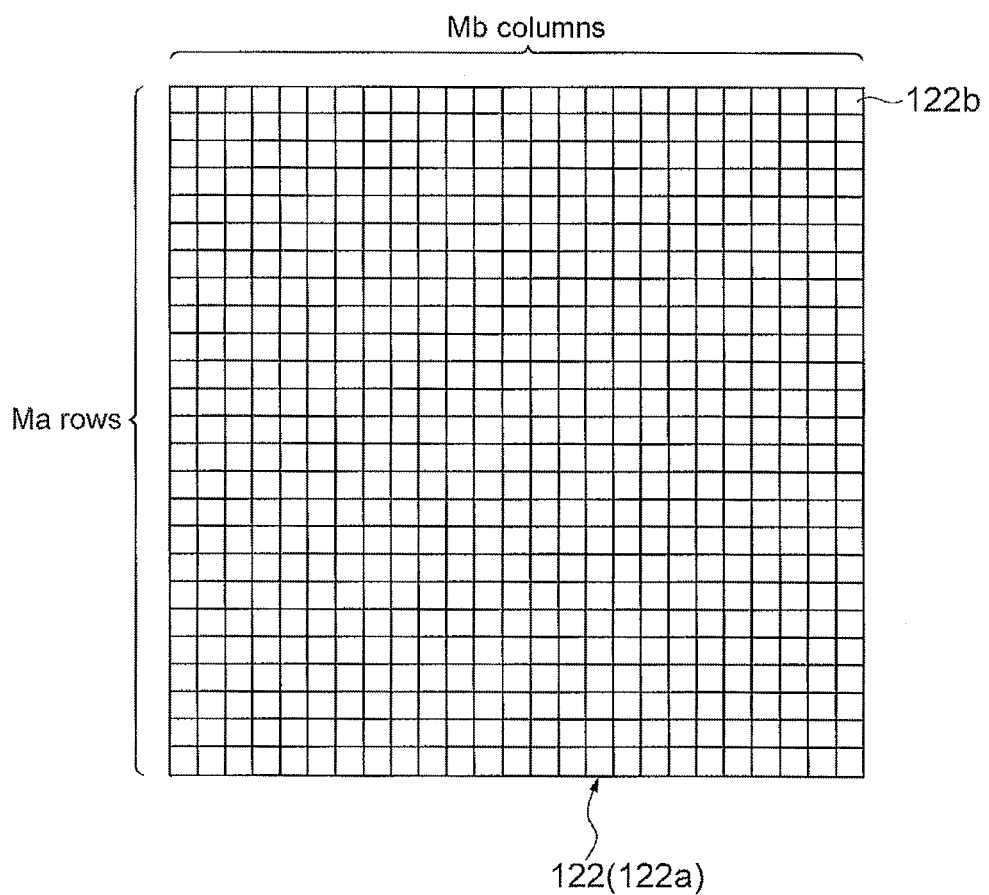
FIG. 4 is a view of an image sensor provided in the wavefront sensor viewed in the optical axis direction of the optical image.

FIG. 2 is a cross-sectional view schematically illustrating a configuration of the wavefront sensor 12 of this embodiment and illustrates a cross section along the optical axis of the optical image La. FIG. 3 is a view of a lens array 120 provided in the wavefront sensor 12 viewed in the optical axis direction of the optical image La. FIG. 4 is a view of an image sensor (optical detection element) 122 provided in the wavefront sensor 12 viewed in the optical axis direction of the optical image La.

Although the wavefront sensor 12 may be of an interference type or a non-interference type, the non-interference type Shack-Hartmann wavefront sensor having the lens array 120 and the image sensor 122 is used as the wavefront sensor 12 in this embodiment. When the non-interference type wavefront sensor is used, there is an advantage in that vibration insensitivity is excellent and a configuration of the wavefront sensor and a process of calculating measurement data can be simpler than when the interference type wavefront sensor is used.

As illustrated in FIG. 3, the lens array 120 has N (N is an integer greater than or equal to 4) lenses 124. The N lenses 124, for example, are arranged in a two-dimensional lattice shape of Na rows and Nb columns (Na and Nb are integers greater than or equal to 2).

Also, the image sensor 122 illustrated in FIG. 2 has a light receiving surface 122a at a position overlapping a back focal plane of the N lenses 124 constituting the lens array 120 and detects a light intensity distribution including N converging spots P formed by the N lenses 124. As illustrated in FIG. 4, the image sensor 122 is configured to include a plurality of pixels 122b arranged in a two-dimensional lattice shape of Ma rows and Mb columns (Ma and Mb are integers greater than or equal to 2). An array pitch of the pixels 122b of the image sensor 122 is configured to be sufficiently less than an array pitch of the lenses 124 so that a magnitude of displacement of a converging image position from the reference position can be detected with high precision.

In the control unit 13 to be described below, a wavefront shape (a distribution of phase gradients) of the optical image La is measured based on a light intensity distribution detected by the image sensor 122. That is, a magnitude of displacement between the position of the converging spot P by the lens 124 and the reference position is proportional to a slope of a local wavefront of the optical image La incident on the lens 124. Accordingly, it is possible to calculate the magnitude of the positional displacement of the converging spot P from the reference position for each lens 124 and measure a wavefront shape of the optical image La based on the positional displacement of the converging spot P.

It is possible to designate a position at which an optical axis of each of the plurality of lenses 124 intersects the light receiving surface 122a of the image sensor 122 as the reference position to be used to calculate the magnitude of the displacement of the converging image position. This position is easily obtained through center-of-gravity calculation using a converging image obtained by causing parallel plane waves to be perpendicularly incident on each lens 124.

The spatial light modulator 11 is an element which receives the optical image La from a light source or an observation object and modulates a wavefront of the optical image La to output the modulated wavefront. Specifically, the spatial light modulator 11 has a plurality of pixels (control points) arranged in a two-dimensional lattice shape and changes a modulation amount (for example, a phase modulation amount) of each pixel according to the control signal S2 provided from the control unit 13. The spatial light modulator 11, for example, includes a liquid crystal on silicon spatial light modulator (LCOS-SLM), a programmable phase modulator (PPM), a liquid crystal display (LCD), micro electro mechanical systems (MEMS), or an electrical address type spatial light modulator formed by coupling an LCD element and an optical address type liquid-crystal spatial light modulator. Also, although the reflection type spatial light modulator 11 is illustrated in FIG. 1, the spatial light modulator 11 may be of a transmission type.

Figure 5:
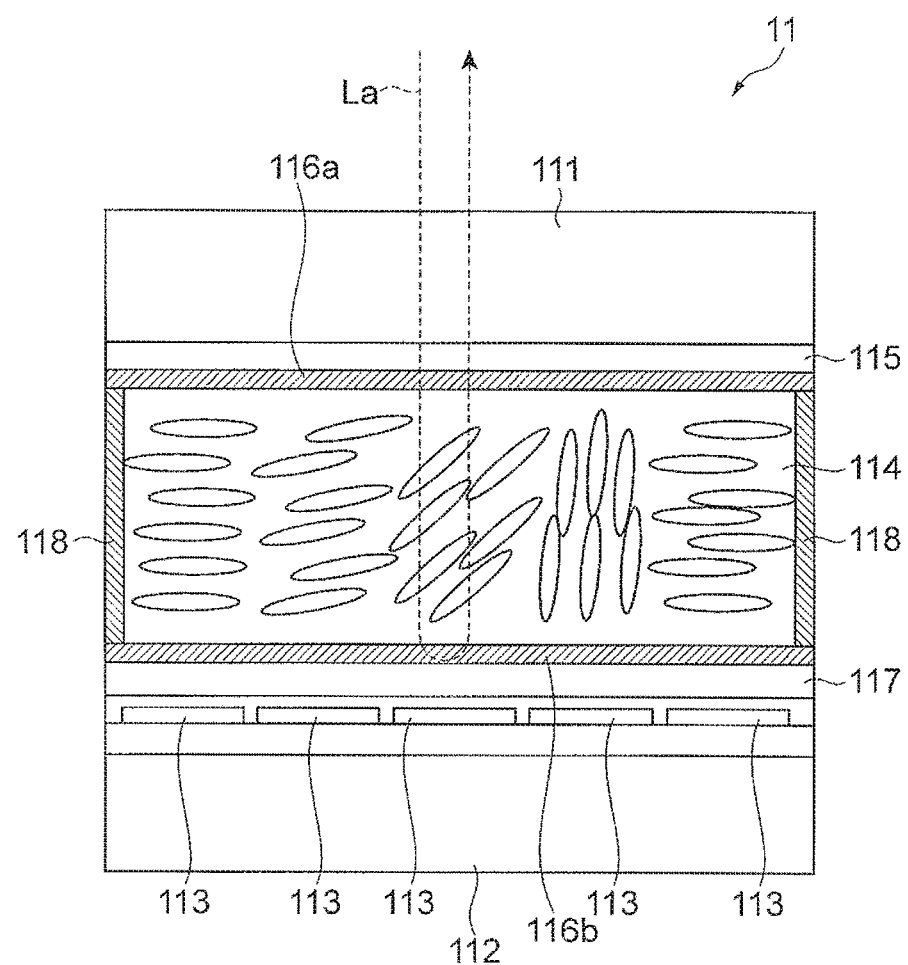
FIG. 5 is a cross-sectional view schematically illustrating an LCOS type spatial light modulator as an example of a spatial light modulator of an embodiment and illustrates a cross section along the optical axis of the optical image.

FIG. 5 is a cross-sectional view schematically illustrating an LCOS type spatial light modulator as an example of the spatial light modulator 11 of this embodiment and illustrates a cross section along the optical axis of the optical image La. This spatial light modulator 11 includes a transparent substrate ill, a silicon substrate 112, a plurality of pixel electrodes 113, a liquid crystal unit (modulation unit) 114, a transparent electrode 115, oriented films 116a and 116b, a dielectric mirror 117, and a spacer 118.

The transparent substrate 111 is formed of a material which transmits the optical image La and arranged along a main surface of the silicon substrate 112. The plurality of pixel electrodes 113 are arranged in a two-dimensional lattice shape on the main surface of the silicon substrate 112 and constitute pixels of the spatial light modulator 11. The transparent electrode 115 is arranged on the surface of the transparent substrate 111 opposite to the plurality of pixel electrodes 113. The liquid crystal unit 114 is arranged between the plurality of pixel electrodes 113 and the transparent electrode 115. The oriented film 116a is arranged between the liquid crystal unit 114 and the transparent electrode 115 and the oriented film 116b is arranged between the liquid crystal unit 114 and the plurality of pixel electrodes 113. The dielectric mirror 117 is arranged between the oriented film 116b and the plurality of pixel electrodes 113. The dielectric mirror 117 reflects the optical image La incident from the transparent substrate 111 and transmitted through the liquid crystal unit 114 and causes the optical image La to be re-emitted from the transparent substrate 111.

Also, the spatial light modulator 11 further includes a pixel electrode circuit (active matrix drive circuit) 119 configured to control a voltage to be applied between the plurality of pixel electrodes 113 and the transparent electrode 115. When the voltage is applied from the pixel electrode circuit 119 to any pixel electrode 113, a refractive index of the liquid crystal unit 114 on the pixel electrode 113 changes according to a magnitude of an electric field generated between the pixel electrode 113 and the transparent electrode 115. Accordingly, an optical path length of the optical image La transmitted through a relevant part of the liquid crystal unit 114 changes and consequently a phase of the optical image La changes. By applying voltages of various magnitudes to the plurality of pixel electrodes 113, it is possible to electrically write a spatial distribution of a phase adjustment amount and implement various wavefront shapes if necessary.

Figure 6:
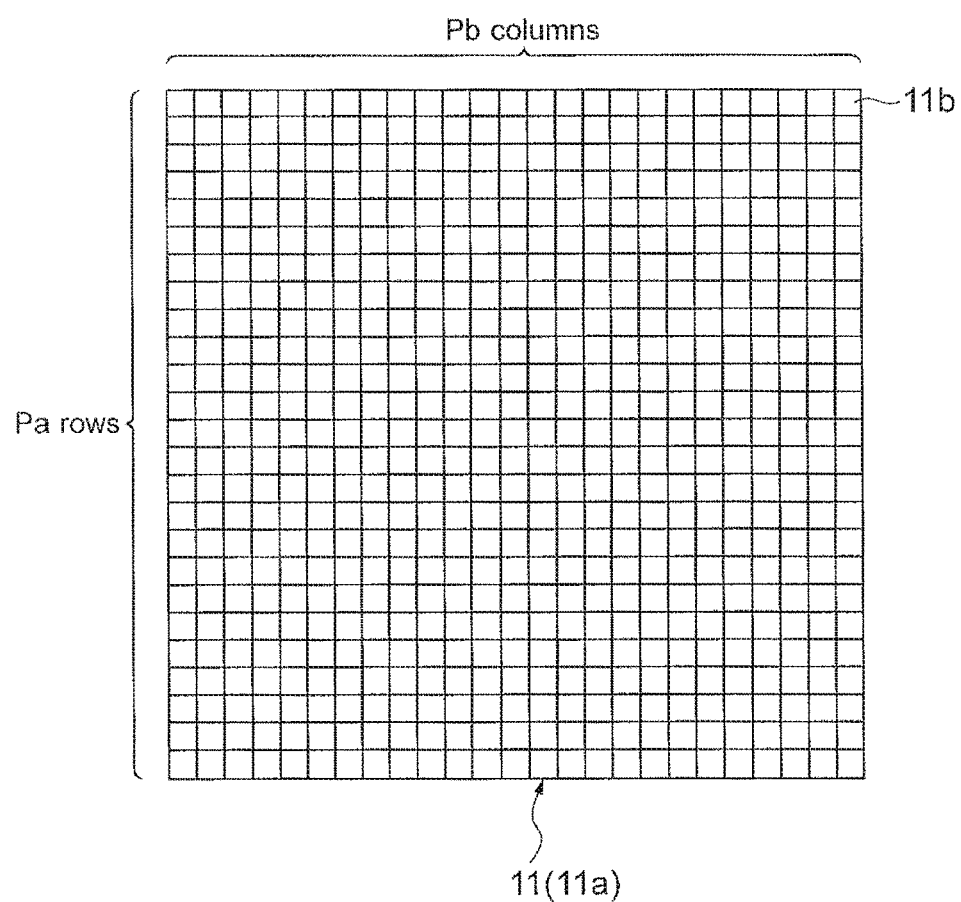
FIG. 6 is a front view of a modulation surface of the spatial light modulator.

FIG. 6 is a front view of a modulation surface 11a of the spatial light modulator 11. As illustrated in FIG. 6, the modulation surface 11a is configured to include a plurality of pixels 11b arranged in a two-dimensional lattice shape of Pa rows and Pb columns (Pa and Pb are integers greater than or equal to 2). Also, each of the plurality of pixels 11b is constituted of one of the plurality of pixel electrodes 113.

Description will now return to FIG. 1. In this adaptive optics system 10, the optical image La from a light source or an observation object (not illustrated) is first incident on the spatial light modulator 11 as substantially parallel light. The optical image La modulated by the spatial light modulator 11 is incident on the beam splitter 14 via the relay lenses 15 and 16 and is branched into two optical images. One optical image La after the branching is incident on the wavefront sensor 12. The data S1 including the wavefront shape (for example, a phase distribution) of the optical image La is generated in the wavefront sensor 12 and the data S1 is provided to the control unit 13. The control unit 13 calculates the wavefront shape (phase distribution) of the optical image La if necessary based on the data S1 from the wavefront sensor 12 and outputs the control signal S2 including the phase pattern for appropriately compensating for wavefront distortion of the optical image La to the spatial light modulator 11. Thereafter, the non-distortion optical image La compensated for by the spatial light modulator 11 is branched by the beam splitter 14 and is incident on the optical detection element 18 via an optical system (not illustrated) and captured.

Here, a coordinate system in the modulation surface 11a of the spatial light modulator 11 and the detection surface of the wavefront sensor 12 is set as follows. That is, two directions parallel to the modulation surface 11a of the spatial light modulator 11 and orthogonal to each other are designated as an x-axis direction and a y-axis direction in the modulation surface 11a and two directions parallel to the detection surface of the wavefront sensor 12 and orthogonal to each other are designated as an x-axis direction and a y-axis direction in the detection surface. However, the x axis in the modulation surface 11a of the spatial light modulator 11 and the x axis in the detection surface of the wavefront sensor 12 are directed to be opposite to each other and the y axis in the modulation surface 11a of the spatial light modulator 11 and the y axis in the detection surface of the wavefront sensor 12 are directed to be opposite to each other. Also, the center of the modulation surface 11a of the spatial light modulator 11 is designated as the origin of the coordinate system in the modulation surface 11a and a point obtained by mapping the center of the modulation surface 11a to the detection surface of the wavefront sensor 12 is designated as the origin of the coordinate system in the detection surface.

At this time, the phase of the wavefront at a position (Xs, Ys) on the modulation surface 11a of the spatial light modulator 11 is mapped one-to-one to the phase of the wavefront at a position (Xc, Yc) on the detection surface of the wavefront sensor 12, and a relation between them is expressed by the following Formulas (1) when there is no angular displacement about the optical axis between the modulation surface 11a and the detection surface.

[Math 1]

$$Xs = \frac{Xc}{M} \quad (1)$$
$$Ys = \frac{Yc}{M}$$

Here, M denotes magnifications of the relay lenses 15 and 16. Also, the magnification M included in Formulas (1) is known in many cases.

However, the angular displacement about the optical axis may occur between the modulation surface 11a and the detection surface of the wavefront sensor 12 due to vibration at the time of transportation or in an installation place or deformation or the like of a member for holding the wavefront sensor or the spatial light modulator by heat. In an angular displacement adjusting method for the adaptive optics system according to this embodiment, a special phase pattern for adjustment is displayed in the spatial light modulator 11 and a feature caused by the phase pattern is detected in the wavefront sensor 12, so that an amount of angular displacement between the wavefront sensor 12 and the modulation surface 11a is acquired. If necessary, angular adjustment between the modulation surface 11a and the wavefront sensor 12 is performed based on the amount of angular displacement.

Hereinafter, a method of detecting the amount of angular displacement between the modulation surface 11a and the wavefront sensor 12 will be described in detail. Also, the detecting method is stored as a program inside a storage region 13a of the control unit 13 illustrated in FIG. 1 and the control unit 13 performs the detecting method by reading the program.

Figure 7:
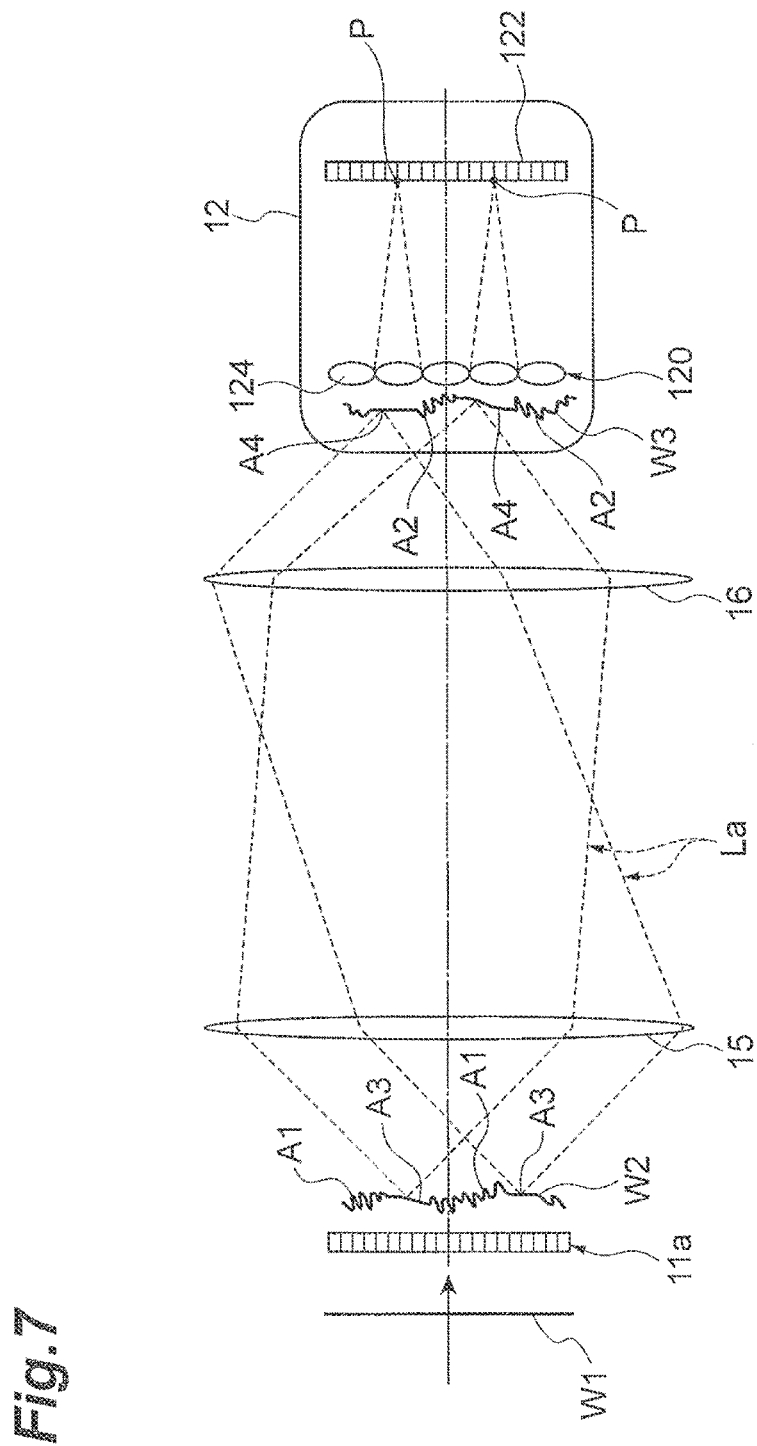
FIG. 7 is a conceptual view illustrating the principle of an adjustment method in an embodiment.

FIG. 7 is a conceptual view illustrating the principle of the detecting method according to this embodiment. In FIG. 7, the relay lenses 15 and 16, a wavefront W1 of an optical image incident on the modulation surface 11a, a wavefront W2 of the optical image emitted from the modulation surface 11a, and a wavefront W3 of the optical image incident on the wavefront sensor 12 are illustrated in addition to the modulation surface 11a of the spatial light modulator 11 and the wavefront sensor 12 (the lens array 120 and the image sensor 122). The wavefront W2 obtained by applying a wavefront according to the phase pattern displayed in the spatial light modulator 11 to the incident wavefront W1 is emitted from the spatial light modulator 11.

The wavefront W3 via a conjugate optical system including the relay lenses 15 and 16 is incident on the wavefront sensor 12. In addition, the optical image La emitted from the region on the modulation surface 11a corresponding to one lens 124 and reaching the lens 124 is illustrated in FIG. 7.

Figure 8:
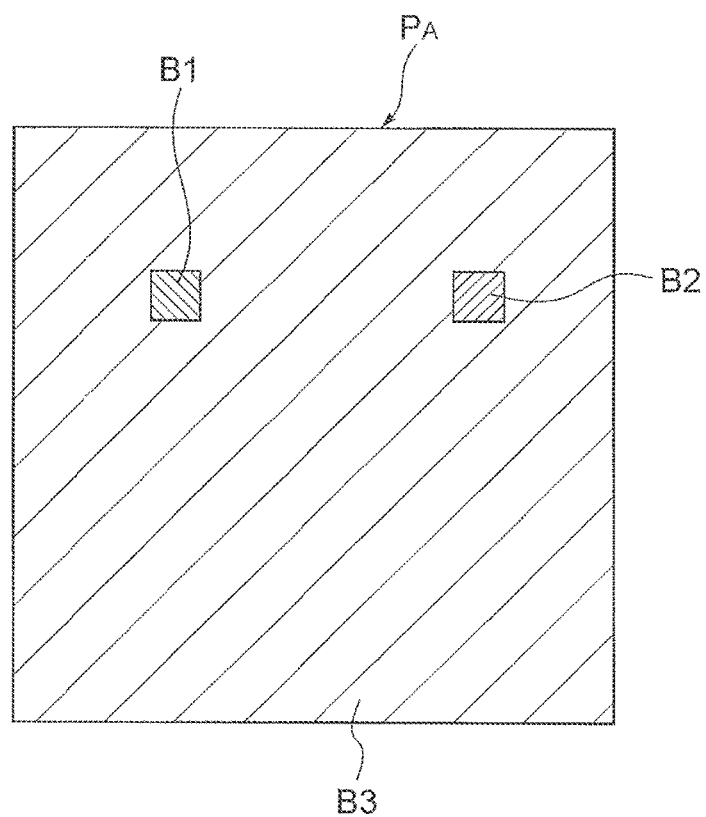
FIG. 8 is a diagram conceptually illustrating a special phase pattern displayed on the modulation surface.

Here, FIG. 8 is a diagram conceptually illustrating a special phase pattern displayed on the modulation surface 11a. As illustrated in FIG. 8, a first phase pattern having linearity in at least one direction is displayed in a first region B1 on the modulation surface 11a having a size corresponding to one lens 124 and a second region B2 on the modulation surface 11a separated from the first region B1 and having a size corresponding to another lens 124. The first phase pattern, for example, is implemented to include a substantially uniform phase distribution, a phase distribution inclined in at least one direction, or the like. Alternatively, the first phase pattern is implemented to include a phase distribution having a cylindrical lens effect in a certain first direction and substantially uniform in a second direction intersecting the first direction or a phase distribution constituting a diffraction grating in the first direction and substantially uniform in the second direction intersecting (for example, orthogonal to) the first direction.

Also, simultaneously, a spatially non-linear second phase pattern (for example, a random distribution in which a distribution of magnitudes of phases is irregular, a defocus distribution which increases a diameter of a converging spot, or the like) is displayed in a region B3 surrounding the first region B1 and the second region B2 on the modulation surface 11a. Then, a wavefront of a part corresponding to the region B3 in the emission wavefront W2 is disturbed (part A1 of FIG. 7). The disturbance of the wavefront occurs even in a part incident on the lens 124 corresponding to the region B3 in the incident wavefront W3 for the wavefront sensor 12 (part A2 of FIG. 7). Thereby, the converging spot P formed by the lens 124 diverges and the converging spot P is not formed, the maximum luminance of the spot is reduced, or a spot diameter is widened. That is, only the converging spot corresponding to the region B3 with degraded clarity can be formed.

On the other hand, the wavefront is incident on the lens 124 without being disturbed in at least one direction according to a first phase pattern having linearity in the at least one direction in parts (parts A3 and A4 of FIG. 7) corresponding to the first and second regions B1 and B2 in the wavefronts W2 and W3. Accordingly, the converging spot P is clearly formed by the lens 124.

Figure 9:
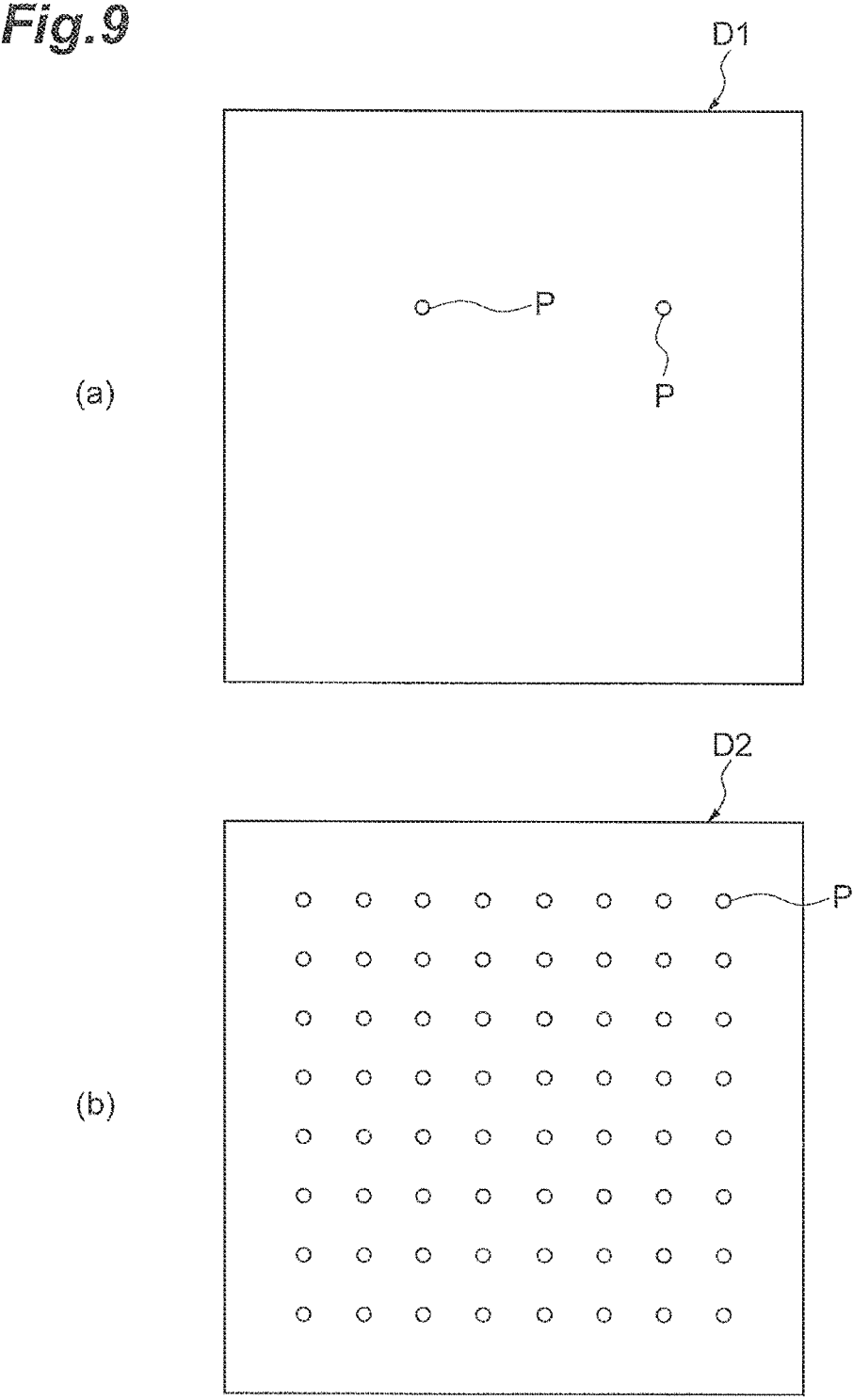
FIG. 9 is a diagram conceptually illustrating light intensity distribution data (Shack-Hartmann-Gram) detected by the image sensor of the wavefront sensor.

FIG. 9 is a diagram conceptually illustrating light intensity distribution data (Shack-Hartmann-Gram) detected by the image sensor 122 of the wavefront sensor 12. FIG. 9(a) illustrates light intensity distribution data D1 of the case in which a phase pattern having linearity in at least one direction is displayed in the regions B1 and B2 and the spatially non-linear phase pattern is displayed in the region B3. FIG. 9(b) illustrates light intensity distribution data D2 of the case in which a phase pattern having linearity in all regions is displayed for comparison.

When the phase pattern having the linearity in all the regions is displayed as illustrated in FIG. 9(b), N converging spots P corresponding to N lenses 124 are included in the light intensity distribution data. On the other hand, when the phase pattern having the linearity in the at least one direction is displayed in the regions B1 and B2 and the spatially non-linear phase pattern is displayed in the region B3 as illustrated in FIG. 9(a), two converging spots P corresponding to the regions B1 and B2 are included in the light intensity distribution data, but the converging spot corresponding to the region B3 is not formed, the maximum luminance of the spot is reduced, or the spot diameter is widened. That is, only the converging spot corresponding to the region B3 with degraded clarity is formed.

Here, FIG. 10 is a diagram conceptually illustrating a relative relation between the modulation surface 11a and the lens array 120. FIG. 10(a) illustrates the case in which there is no angular displacement between the modulation surface 11a and the wavefront sensor 12, that is, the case in which an arrangement direction of the modulation surface 11a and an arrangement direction of the lens 124 (indicated by a broken line in the drawing) are aligned. In this case, N regions 11c (indicated by a bold line in the drawing) in the modulation surface 11a correspond to the N lenses 124. Also, the plurality of pixels 11b are included in each region 11c.

In contrast, when angular displacement occurs between the modulation surface 11a and the wavefront sensor 12, displacement occurs at relative positions between the N regions 11c of the modulation surface 11a and the N lenses 124 as illustrated in FIG. 10(b). The optical image La from the region 11c separated from the center of the angular displacement is incident on another lens 124 different from the lens 124 corresponding to the region 11c.

Figure 11:
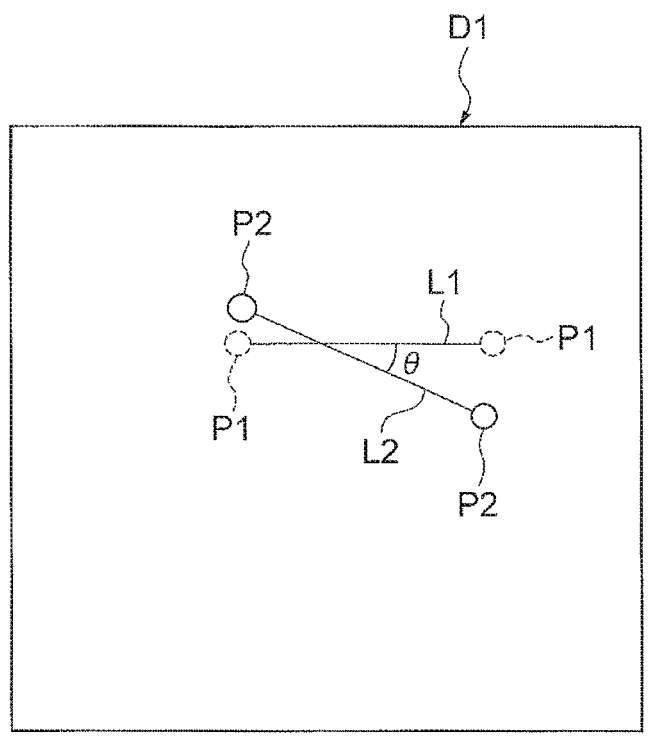
FIG. 11 is a diagram illustrating a state of a position change in a converging spot of the light intensity distribution data due to angular displacement between the modulation surface and the wavefront sensor.

The light intensity distribution data D1 illustrated in FIG. 9(a) changes as follows due to such angular displacement. FIG. 11 is a diagram illustrating a state of a position change in a converging spot P of the light intensity distribution data D1 due to angular displacement between the modulation surface 11a and the wavefront sensor 12. When there is no angular displacement between the modulation surface 11a and the wavefront sensor 12, the two converging spots P1 corresponding to the regions B1 and B2 are formed at predetermined positions. However, when the angular displacement occurs between the modulation surface 11a and the wavefront sensor 12, the two converging spots P2 corresponding to the regions B1 and B2 are formed at different positions from the above-described converging spots P1 as illustrated in FIG. 11.

A relative positional relation between two converging spots P2 is uniquely defined according to an amount of angular displacement between the modulation surface 11a and the wavefront sensor 12. Specifically, an angle θ formed by a line segment L1 connecting the two converging spots P1 and a line segment L2 connecting the two converging spots P2 matches the amount of angular displacement between the modulation surface 11a and the wavefront sensor 12. Therefore, it is possible to know the amount θ of angular displacement between the modulation surface 11a and the wavefront sensor 12 by investigating the relative positional relation between the converging spot P corresponding to the region B1 and the converging spot P corresponding to the region B2 included in the light intensity distribution data D1. Also, the angular displacement amount θ is calculated according to the following Formula (2).

[Math 2]

$$\theta = \arccos\left(\frac{\vec{a} \cdot \vec{b}}{|\vec{a}||\vec{b}|}\right) \quad (2)$$

Here, $\vec{a}$ and $\vec{b}$ denote direction vectors of the line segments L1 and L2. In addition, the angular displacement amount θ may be calculated by substituting a direction vector of a line segment connecting the centers of the regions B1 and B2 into the direction vector $\vec{a}$ of the line segment L1.

Here, an example of a "spatially non-linear second phase pattern" displayed in the region B3 of FIG. 8 is shown. FIGS. 12 to 15 are diagrams illustrating examples of such a phase pattern, wherein a magnitude of a phase is shown according to light and shade, a phase of a darkest part is 0 (rad), and a phase of a brightest part is 2π (rad).

Figure 12:
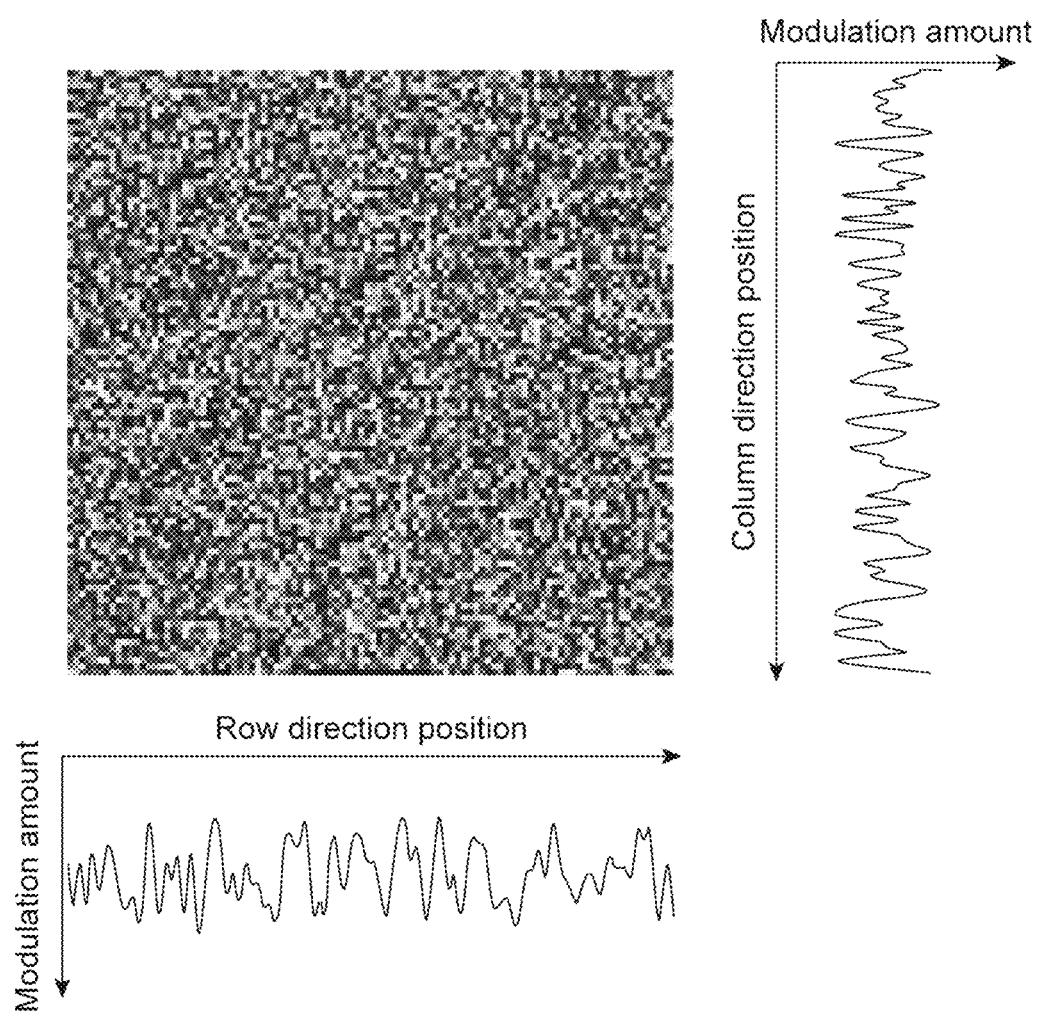
FIG. 12 is a diagram illustrating a random distribution in which a distribution of magnitudes of phases is irregular as an example of a spatially non-linear phase pattern.
Figure 13:
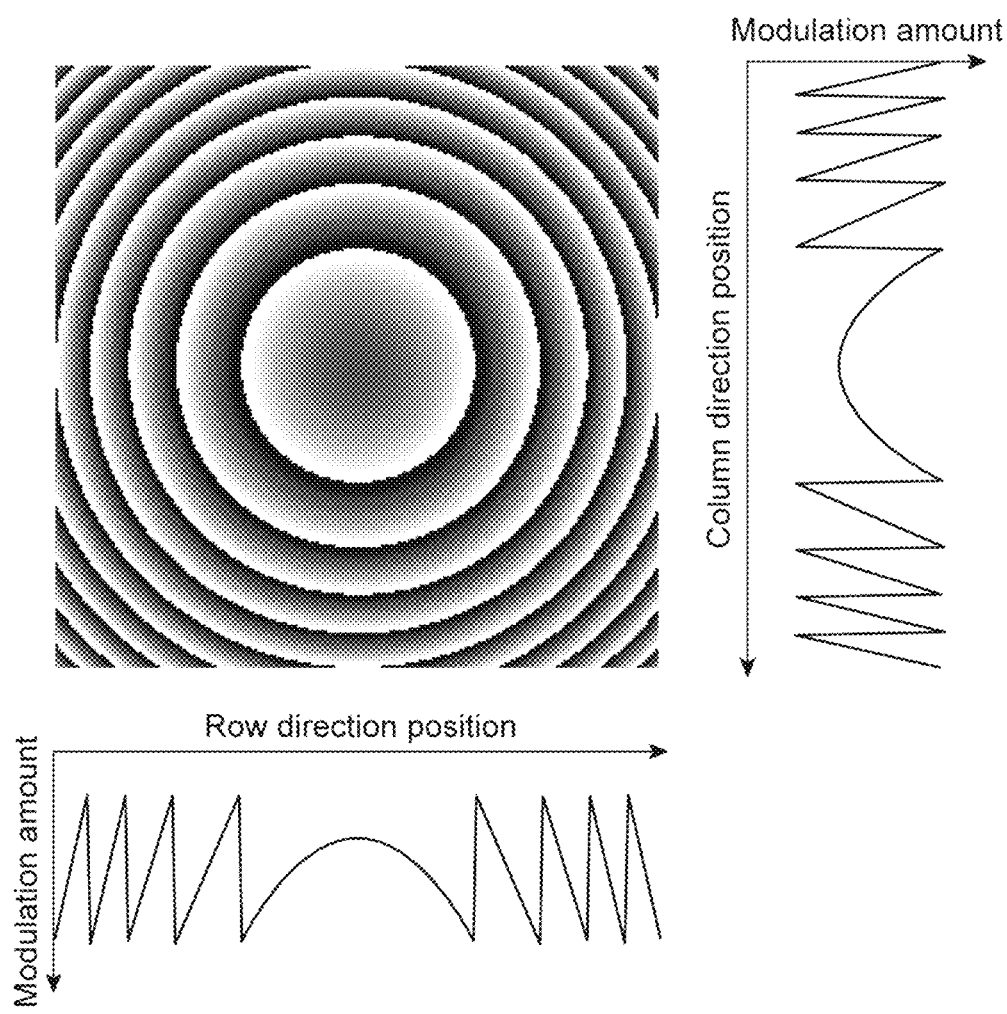
FIG. 13 is a diagram illustrating a defocus distribution which increases a diameter of a converging spot as an example of the spatially non-linear phase pattern.
Figure 14:
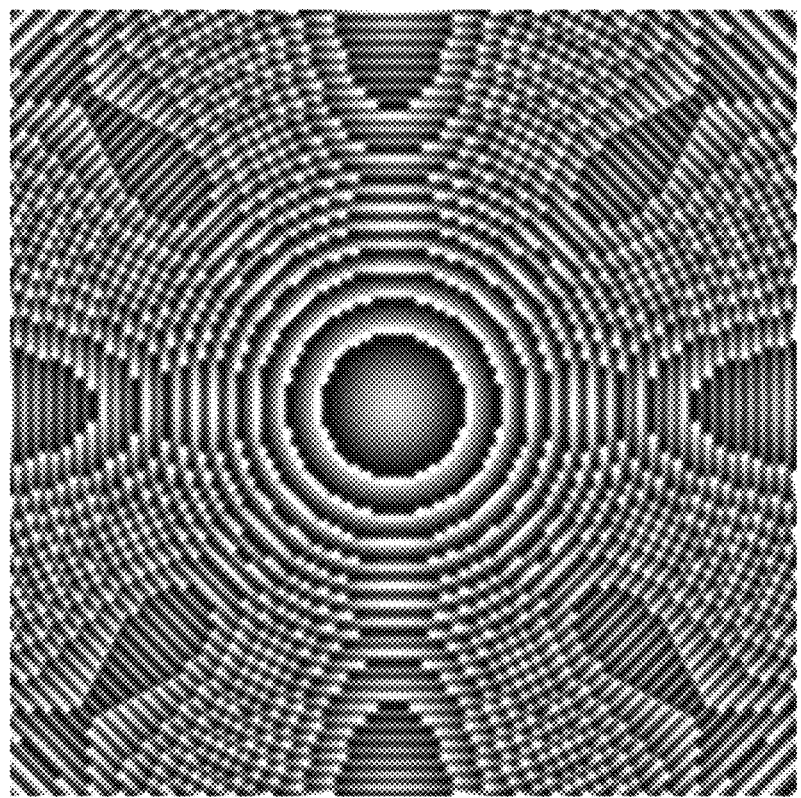
FIG. 14 is a diagram illustrating a distribution which causes a large spherical aberration in an optical image as an example of the spatially non-linear phase pattern.
Figure 15:
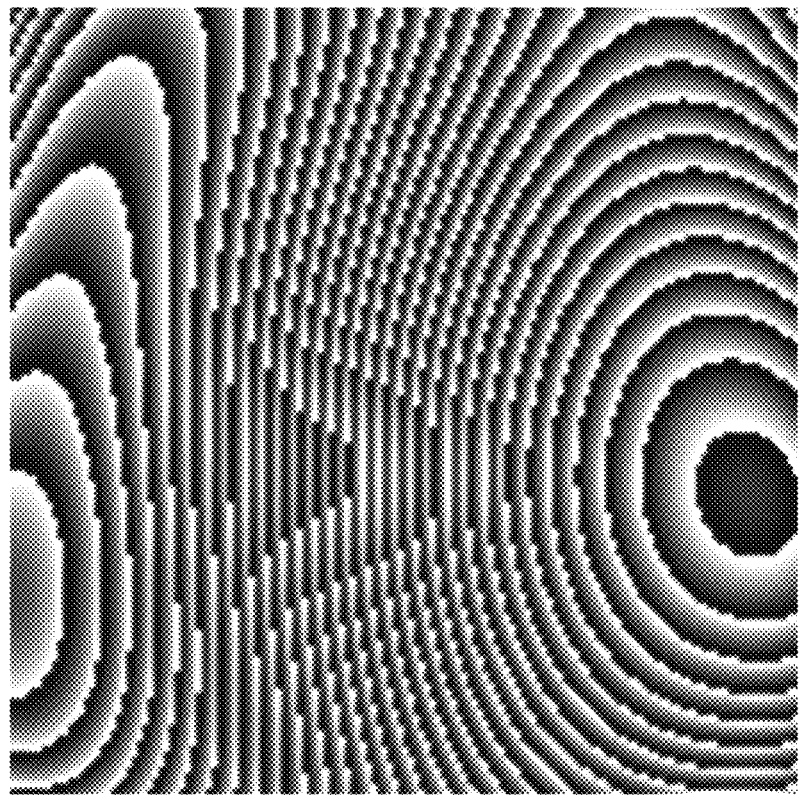
FIG. 15 is a diagram illustrating a distribution which causes an aberration including a high-order aberration in the optical image as an example of the spatially non-linear phase pattern.

FIG. 12 illustrates a random distribution in which a distribution of magnitudes of phases is irregular. Also, an example in which a graph of a phase modulation amount at one position of each of row and column directions is also illustrated in FIG. 12. When this phase pattern is displayed in the region B3, the optical image La of a relevant part diverges and a clear converging spot P is not formed. FIG. 13 illustrates a defocus distribution which increases a diameter of a converging spot P. Even in FIG. 13, an example of a graph of a phase modulation amount at one position of each of row and column directions is illustrated. When such a phase pattern is displayed in the region B3, a clear converging spot P is not formed because the optical image La of the relevant part is conversely widened without converging. FIG. 14 illustrates a distribution which causes a large spherical aberration in the optical image La. FIG. 15 illustrates a distribution which causes an aberration including a large high-order aberration in the optical image La. Even when the phase pattern illustrated in FIG. 14 or 15 is displayed in the region B3, the clear converging spot P is not formed. The spatially non-linear second phase pattern may include at least one of the above-described distributions or may include a composite pattern in which at least one of the above-described distributions and a linear phase pattern are superimposed.

Figure 16:
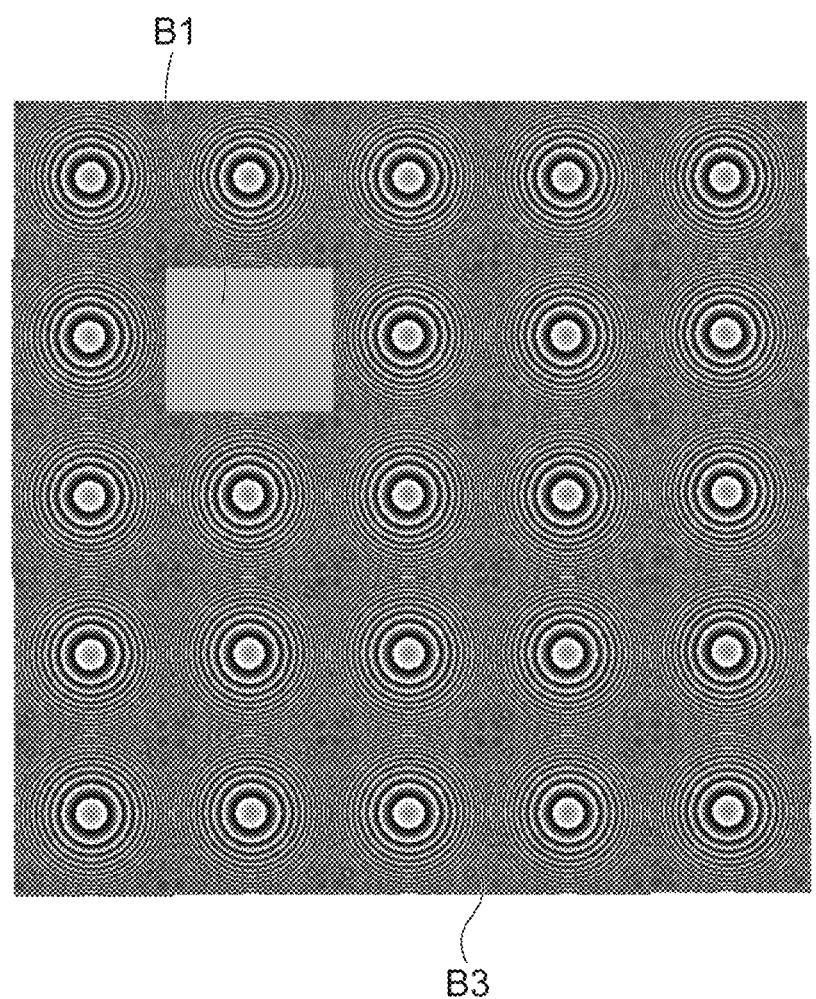
FIG. 16 illustrates an example of a phase pattern in which a common phase distribution (for example, a defocus distribution) is arranged for every two or more regions.
Figure 17:
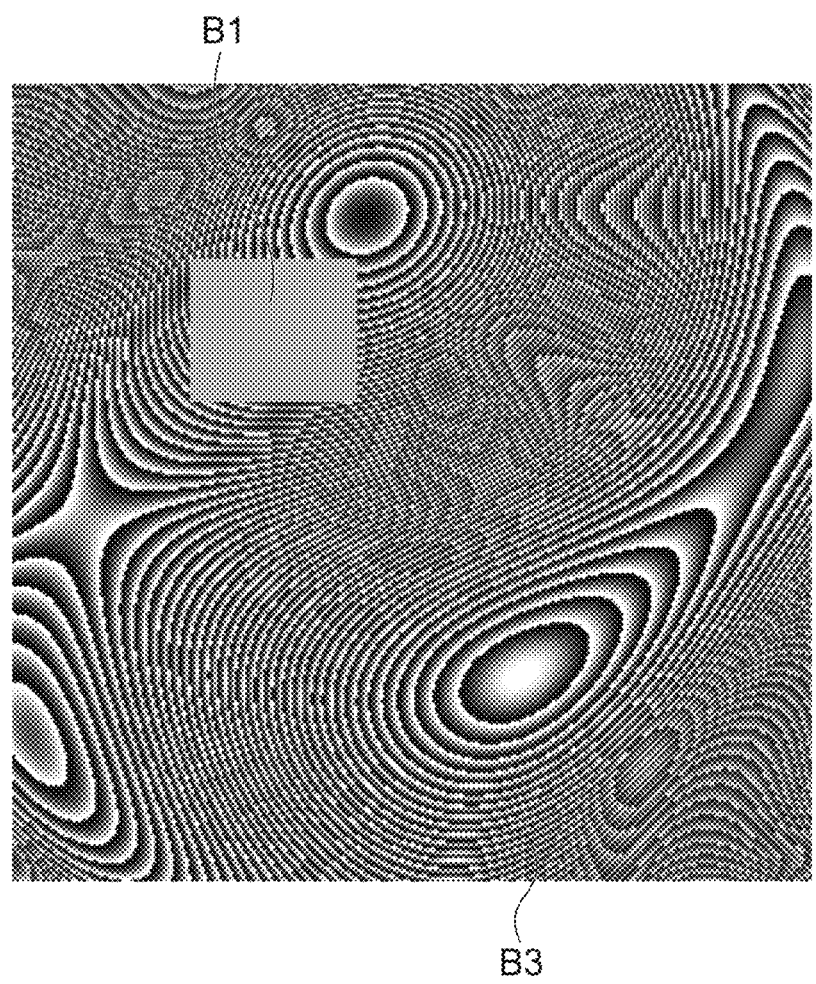
FIG. 17 illustrates an example of a phase pattern in which different phase distributions (for example, phase distributions in which an aberration including a high-order aberration is caused) are arranged for every two or more regions.

Also, the non-linear second phase pattern displayed in the region B3 may include a common phase distribution for every two or more regions formed by dividing the region B3 and may include different phase distributions for every two or more regions formed by dividing the region B3. FIG. 16 illustrates an example of a phase pattern in which a common phase distribution (for example, a defocus distribution) is arranged for every two or more regions formed by dividing the region B3. Also, FIG. 17 illustrates an example of a phase pattern in which different phase distributions (for example, phase distributions which cause an aberration including a high-order aberration) are arranged for every two or more regions formed by dividing the region B3.

Figure 18:
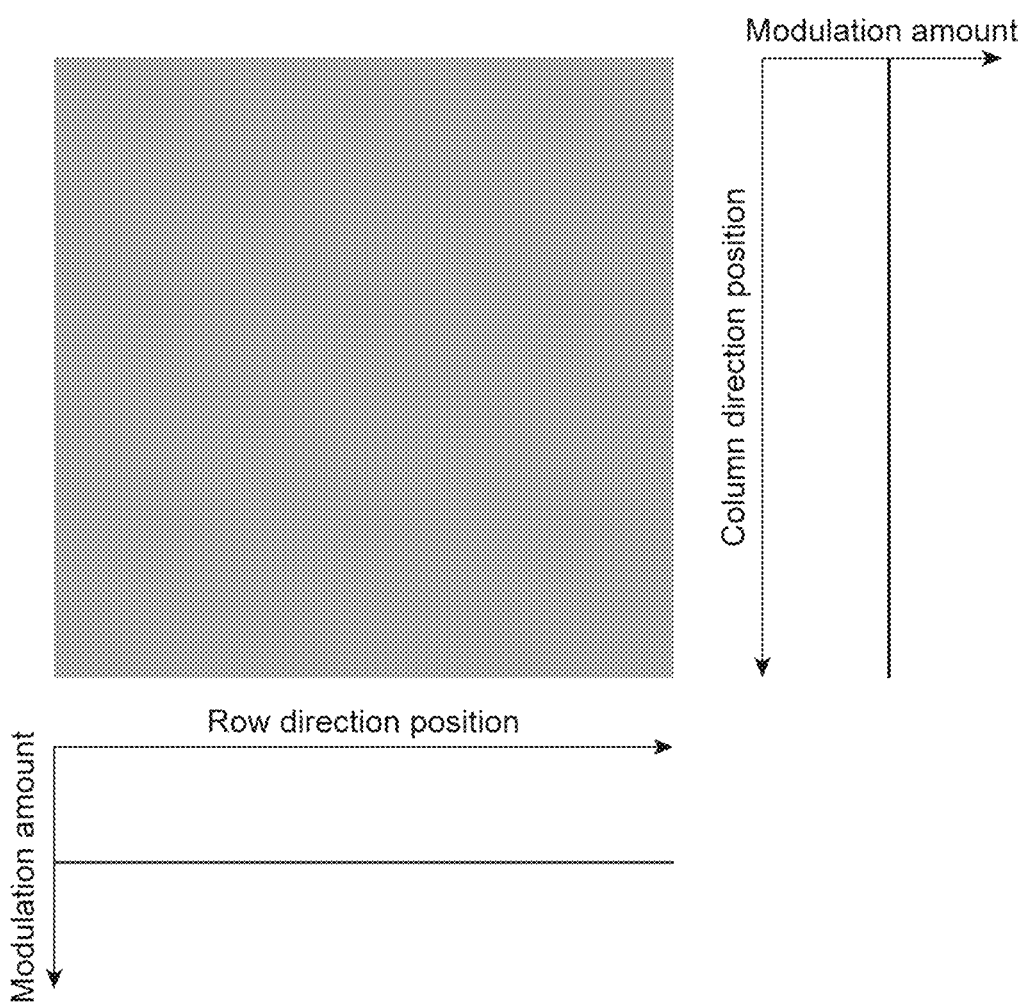
FIG. 18 is a diagram illustrating a phase distribution in which phase values are substantially uniform across the entire surface of the modulation surface as an example of a phase pattern having linearity in at least one direction.

A "first phase pattern having linearity in at least one direction" displayed in the regions B1 and B2 of FIG. 8, for example, is implemented by a phase distribution in which phase values are substantially uniform across the entire surface of the modulation surface 11a. FIG. 18 is a diagram illustrating such a phase pattern, wherein the magnitude of the phase is indicated by light and shade as in FIGS. 12 to 17. Because the wavefront of the optical image La of the relevant part is flat when the phase pattern as illustrated in FIG. 18 is displayed in the regions B1 and B2, the clear converging spot P is formed by the lens 124.

Figure 19:
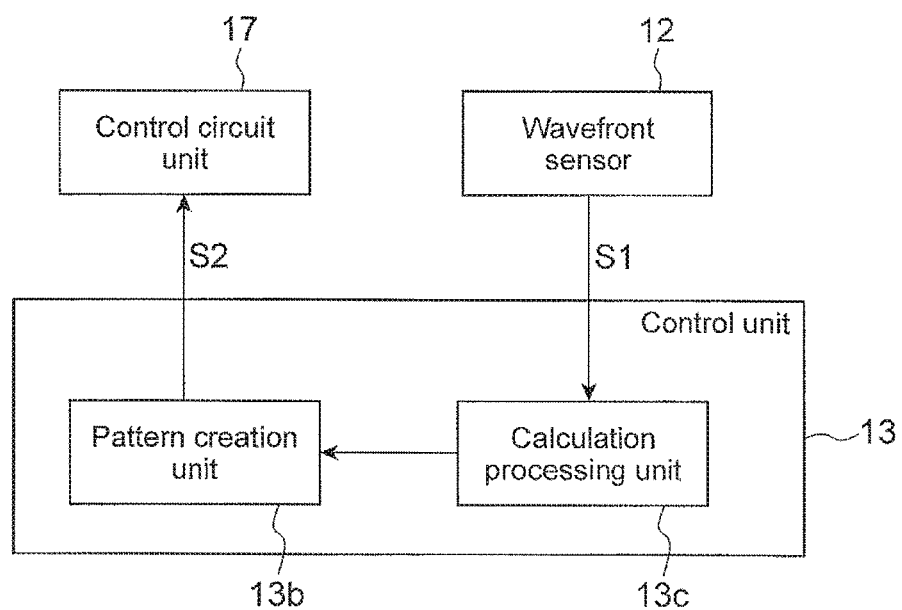
FIG. 19 is a block diagram illustrating an example of an internal configuration of a control unit.

FIG. 19 is a block diagram illustrating an example of an internal configuration of the control unit 13 of this embodiment. The control unit 13 can be configured to include a pattern creation unit 13b and a calculation processing unit 13c. Also, the pattern creation unit 13b and the calculation processing unit 13c are stored as a program inside the storage region 13a of the control unit 13 illustrated in FIG. 1 and implemented by the control unit 13 reading and executing the program.

The pattern creation unit 13b creates a special phase pattern for detecting an amount of angular displacement between the modulation surface 11a and the wavefront sensor 12, that is, a phase pattern including the regions B1 to B3. Also, the phase pattern is sent as a control signal S2 from the pattern creation unit 13b to the control circuit unit 17.

Here, a special phase pattern PA for detecting the angular displacement amount, for example, is expressed by the following Formula (3).

[Math 3]

$$P_A(n, m) = \begin{cases} a & (n, m) \subset ROI \\ rand() & (n, m) \not\subset ROI \end{cases} \quad (3)$$

Here, a denotes a certain constant and is an example of a first phase pattern having linearity in at least one direction. Also, rand( ) denotes a random function and is an example of a spatially non-linear second phase pattern. (n, m) denotes coordinates in units of pixels on the modulation surface 11a. ROI is defined as a reference sign denoting the regions B1 and B2.

As described above, each of the regions B1 and B2 in this embodiment has a size corresponding to one lens 124. When the plurality of lenses 124 are arranged in a two-dimensional lattice shape as illustrated in FIG. 3 in the lens array 120, shapes of the regions B1 and B2 become squares. Accordingly, the above Formula (3) can be modified as in the following Formula (4).

[Math 4]

$$P_A(n, m) = \begin{cases} a & |n - xc_1| \le \frac{w}{2}, |m - yc_1| \le \frac{w}{2} \\ a' & |n - xc_2| \le \frac{w}{2}, |m - yc_2| \le \frac{w}{2} \\ rand() & (n, m) \not\subset ROI \end{cases} \quad (4)$$

Here, $(xc_1, yc_1)$ is center coordinates of the region B1, $(xc_2, yc_2)$ is center coordinates of the region B2, w is the number of pixels of one side of the region B1 or B2, and a' is the same constant as the constant a or a different constant from the constant a. Also, assuming that an array pitch of the pixels 11b in the modulation surface 11a is denoted by slmPITCH, an array pitch of the lenses 124 in the lens array 120 is denoted by mlaPITCH, and imaging magnification of an optical system between the modulation surface 11a and the lens surface of the lens array 120 is denoted by M, the number of pixels w of one side of the region B1 or B2 is expressed by the following Formula (5).

[Math 5]

$$w = \frac{1}{M} \times \frac{mlaPITCH}{slmPITCH} \quad (5)$$

In other words, a width (=w×slmPITCH) of the region B1 or B2 in an array direction of the plurality of lenses 124 is (1/M) times the array pitch mlaPITCH of the plurality of lenses 124.

When the above-described phase pattern $P_A$ is displayed on the modulation surface 11a, the calculation processing unit 13c acquires the light intensity distribution data S1 output from the wavefront sensor 12. The calculation processing unit 13c calculates a center of gravity position of each converging spot P included in the light intensity distribution data S1 according to an algorithm that will be described below. The calculation processing unit 13c calculates an amount of angular displacement between the modulation surface 11a and the wavefront sensor 12 based on the center of gravity position of the converging spot P corresponding to the region B1 and the center of gravity position of the converging spot P corresponding to the region B2.

Figure 20:
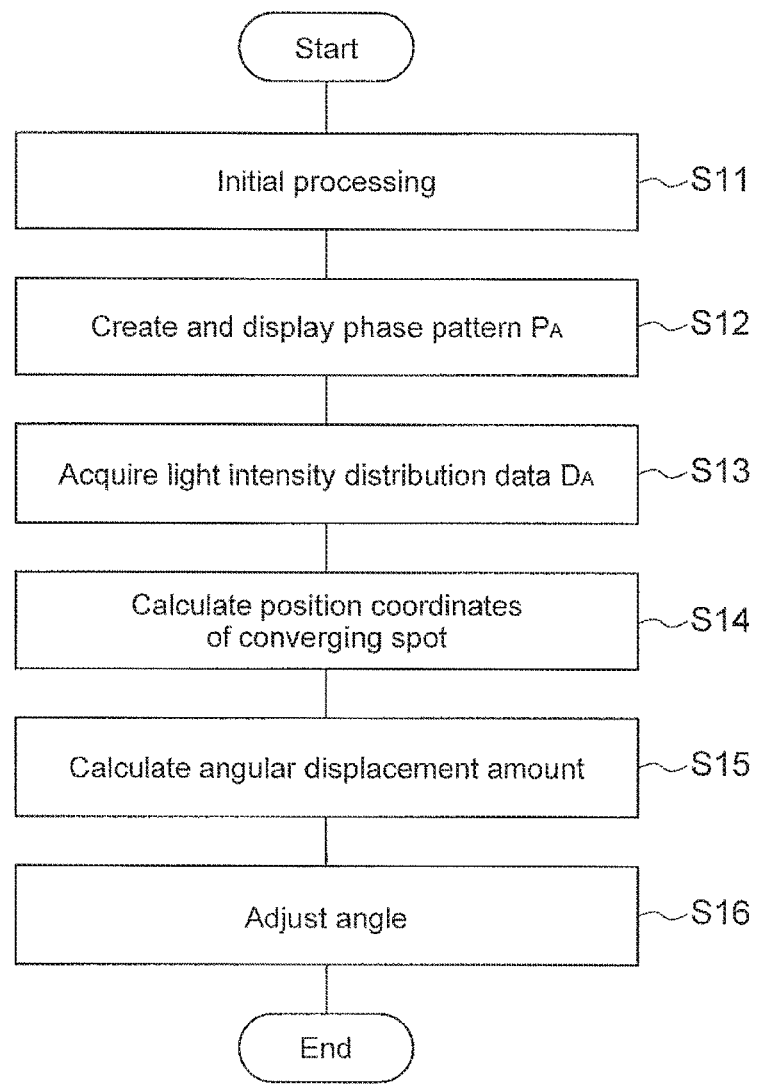
FIG. 20 is a flowchart illustrating an angular displacement detecting method and an operation of an adaptive optics system according to a first embodiment.

An operation of the adaptive optics system 10 including detection of the amount of angular displacement between the modulation surface 11a and the wavefront sensor 12 described above will be described with reference to FIG. 20. FIG. 20 is a flowchart illustrating the operation and angular displacement detecting method of the adaptive optics system 10 of this embodiment. Also, the angular displacement detecting method is stored as a program for the adaptive optics system inside the storage region 13a of the control unit 13 illustrated in FIG. 1 and the control unit 13 executes the angular displacement detecting method by reading the program.

In the adaptive optics system 10, initial processing of the control unit 13 is first performed (step S11). In this initial processing step S11, for example, the securement of a memory region necessary for a calculation process, initial setting of parameters, etc. are performed. Also, in step S11, the center of the region B1 or B2 may be designated in any pixel of the modulation surface 11a as the initial processing of the special phase pattern $P_A$ for detecting the angular displacement amount.

Next, the control unit 13 creates the special phase pattern $P_A$ for detecting the angular displacement amount and displays the created special phase pattern $P_A$ on the modulation surface 11a (step S12). In this step S12, the phase pattern (for example, see FIG. 18) having linearity in at least one direction is displayed in the regions B1 and B2 on the modulation surface 11a corresponding to two lenses 124 of the plurality of lenses 124 of the lens array 120 and the spatially non-linear phase pattern (for example, see FIGS. 12 to 15) is displayed in the region B3 surrounding the regions B1 and B2.

Subsequently, the control unit 13 acquires the light intensity distribution data (hereinafter referred to as light intensity distribution data $D_A$) through the image sensor 122 in a state in which the above-described phase pattern $P_A$ is displayed (step S13, light intensity distribution acquiring step).

Subsequently, the control unit 13 specifies position coordinates of each converging spot P by calculating centers of gravity of two converging spots P included in the light intensity distribution data $D_A$ (step S14). Position coordinates (xp, yp) of the converging spot P are expressed by the following Formulas (6). Also, $A_{ij}$ denotes a light intensity at coordinates (i, j) of the light intensity distribution data $D_A$ and R0 denotes a calculation target region in which the converging spot P can be present in the image sensor 122.

[Math 6]

$$xp = \frac{\sum_{i,j \subset R_0} iA_{ij}}{\sum_{i,j \subset R_0} A_{ij}} \quad (6)$$

$$yp = \frac{\sum_{i,j \subset R_0} jA_{ij}}{\sum_{i,j \subset R_0} A_{ij}}$$

Also, before the center of gravity is calculated, processing of a threshold value, noise reduction, or the like may be performed in the light intensity distribution data $D_A$.

Subsequently, the control unit 13 calculates an amount of angular displacement between the modulation surface 11a and the wavefront sensor 12 according to the principle illustrated in FIG. 11 based on a relative relation between position coordinates of two converging spots P calculated in step S14 (step S15, angle calculation step).

Thereafter, the control unit 13 may adjust an angle around the optical image La of at least one of the modulation surface 111a and the wavefront sensor 12 so that the angular displacement amount calculated in step S15 is reduced (step S16, adjusting step). This adjustment, for example, is performed by adjusting one or both of a mounting angle of the spatial light modulator 11 and a mounting angle of the wavefront sensor 12. In addition, because the correspondence relation between the regions B1 and B2 and the two converging spots P is normally eliminated by this angular adjustment, the above-described steps S12 to S16 may be iterated. If the angular displacement amount calculated in step S15 is substantially zero, the angular displacement is completed.

Effects obtained by the angular displacement detecting method for the adaptive optics system 10 and the adaptive optics system 10 according to this embodiment described above will be described. In this embodiment, in the light intensity distribution acquiring step S13, the light intensity distribution data DA is acquired by the image sensor 122 of the wavefront sensor 12 in a state in which the phase pattern having linearity in at least one direction is displayed in the regions B1 and B2 of the spatial light modulator 11 and the spatially non-linear phase pattern is displayed in the region B3 surrounding the regions B1 and B2. In the light intensity distribution data DA, the converging spots P corresponding to the regions B1 and B2 are formed, but the relative positional relation between the converging spots P changes according to the amount of angular displacement between the modulation surface 11a and the wavefront sensor 12. Accordingly, it is possible to detect the amount of angular displacement between the modulation surface 11a and the wavefront sensor 12 based on the relative positional relation between the converging spots P corresponding to the regions B1 and B2.

Also, in this embodiment, it is possible to easily and quickly detect the amount of angular displacement according to only an operation of the control unit 13 without requiring the special component or structure for detecting the angular displacement amount. Also, in the method disclosed in the above-described Non Patent Literature 2, the phase pattern structure is complex and not easy to create. On the other hand, in this embodiment, it is only necessary for the phase pattern $P_A$ to include the regions B1 to B3 formed of a simple phase pattern, a structure of the phase pattern is easy, and the creation of the phase pattern by the control unit 13 is also easy. In addition, in the method disclosed in Non Patent Literature 2, it is necessary to calculate the entire wavefront shape based on the light intensity distribution data output from the wavefront sensor 12. On the other hand, the calculation process is facilitated because the angular displacement amount can be detected based on only a part of the light intensity distribution data in this embodiment.

As described above, it is possible to easily detect an amount of angular displacement about the optical axis between the modulation surface 11a and the wavefront sensor 12 and perform angular adjustment according to the angular displacement detecting method of this embodiment and the adaptive optics system 10.

Also, the sizes of the regions B1 and B2 are set so that the size of a wavefront part A4 (see FIG. 7) matches a diameter of the lens 124 (see Formula (5)) in this embodiment. However, the sizes of the regions B1 and B2 are not limited thereto, and, for example, may be set so that a length of one side of the wavefront part A4 becomes $n_1$ ($n_1$ is a natural number) times the diameter of the lens 124. In this case, assuming that an array pitch of the pixels 11b in the modulation surface 11a is denoted by slmPITCH, an array pitch of the lenses 124 in the lens array 120 is denoted by mlaPITCH, and imaging magnification of an optical system between the modulation surface 11a and the lens surface of the lens array 120 is denoted by M, the number of pixels w of one side of the region B1 or B2 is expressed by the following Formula (7).

[Math 7]

$$w = \frac{n_1}{M} \times \frac{mlaPITCH}{slmPITCH} \qquad (7)$$

In other words, a width (=w×slmPITCH) of the region B1 or B2 in an array direction of the plurality of lenses 124 can be ($n_1$/M) times the array pitch mlaPITCH of the plurality of lenses 124.

(Second Embodiment)

In the above-described first embodiment, the light intensity distribution data $D_A$ is acquired in a state in which the first phase pattern having linearity in at least one direction is displayed in the regions B1 and B2 in the light intensity distribution acquiring step S13. However, it is not necessarily necessary to simultaneously display the first phase pattern to be displayed in the regions B1 and B2, and the above-described embodiment can be modified as follows.

Figure 21:
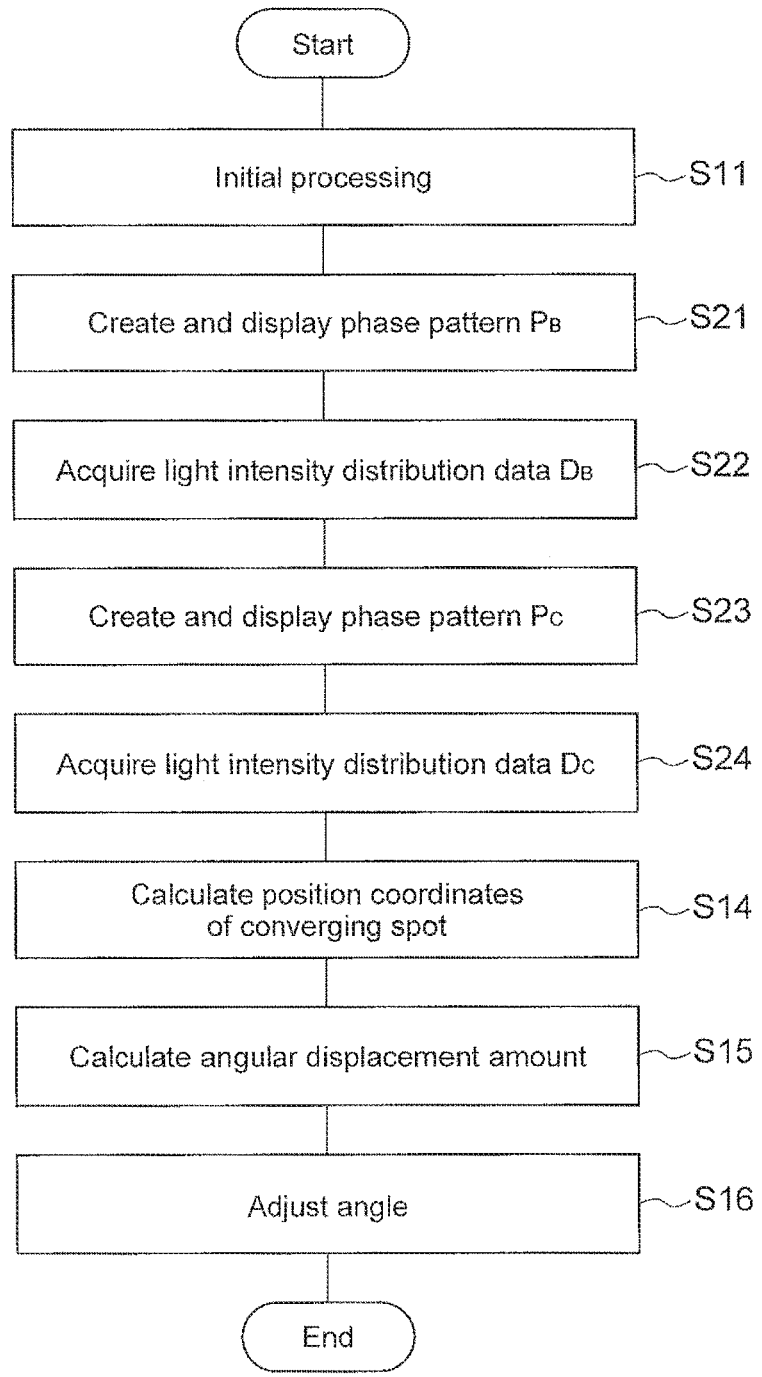
FIG. 21 is a flowchart illustrating an angular displacement detecting method and an operation of a control unit according to a second embodiment.

FIG. 21 is a flowchart illustrating an angular displacement detecting method and an operation of a control unit 13 according to the second embodiment. A difference between this embodiment and the above-described first embodiment is that steps S21 to S24 are provided instead of steps S12 and S13 illustrated in FIG. 20. Also, because the other steps are similar to those of the above-described first embodiment, detailed description thereof will be omitted.

Figure 22:
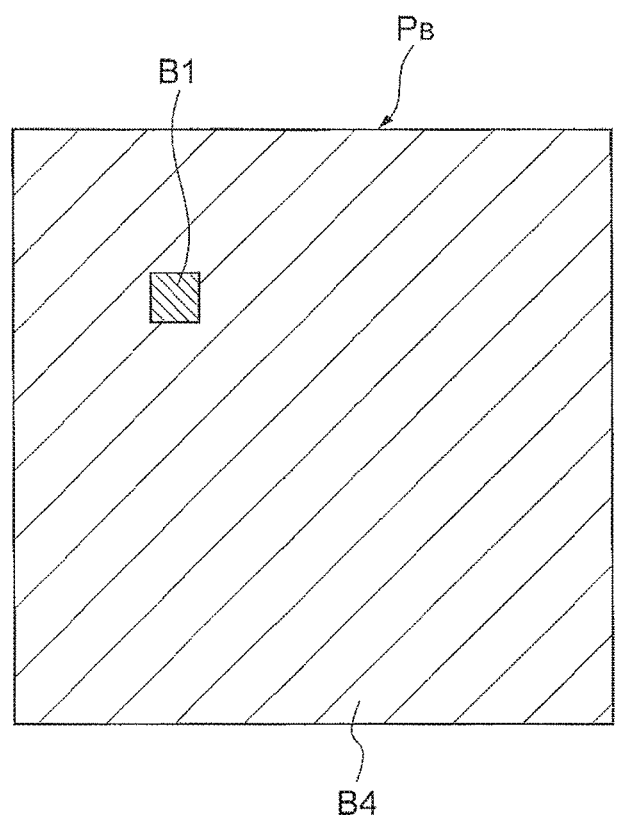
FIG. 22 is a diagram conceptually illustrating a phase pattern of a first modified example.

In step S21, the control unit 13 creates a special phase pattern $P_B$ for detecting an angular displacement amount and displays the created special phase pattern $P_B$ on the modulation surface 11a. FIG. 22 is a diagram conceptually illustrating the phase pattern $P_B$ of this modified example. As illustrated in FIG. 22, in the phase pattern $P_B$, the first phase pattern (for example, see FIG. 18) having linearity in at least one direction is displayed in the first region B1 on the modulation surface 11a. Also, simultaneously, a spatially non-linear second phase pattern (for example, see FIGS. 12 to 15) is displayed in a region B4 surrounding the first region B1 on the modulation surface 11a.

Subsequently, in step S22, the control unit 13 acquires the first light intensity distribution data (hereinafter referred to as light intensity distribution data $D_B$) through the image sensor 122 in a state in which the above-described phase pattern $P_B$ is displayed (first light intensity distribution acquiring step). In this first light intensity distribution data $D_B$, a converging spot P corresponding to the region B1 is included.

Figure 23:
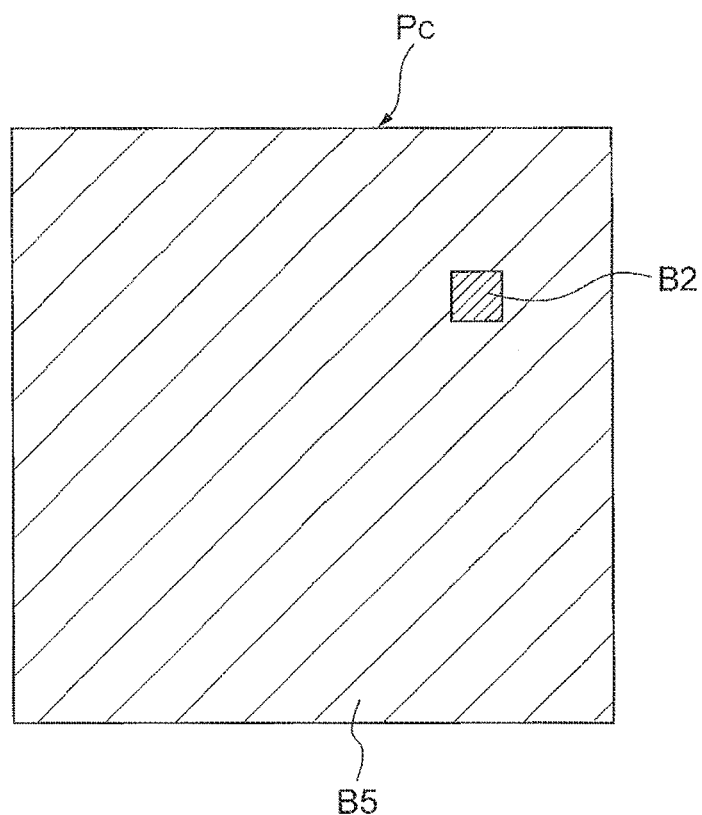
FIG. 23 is a diagram conceptually illustrating another phase pattern of the first modified example.

Subsequently, in step S23, the control unit 13 creates a special phase pattern $P_C$ for detecting an angular displacement amount and displays the created special phase pattern $P_C$ on the modulation surface 11a. FIG. 23 is a diagram conceptually illustrating the phase pattern $P_C$ of this modified example. As illustrated in FIG. 23, in the phase pattern $P_C$, the first phase pattern (for example, see FIG. 18) having linearity in at least one direction is displayed in the second region B2 on the modulation surface 11a. Also, simultaneously, a spatially non-linear second phase pattern (for example, see FIGS. 12 to 15) is displayed in a region B5 surrounding the second region B2 on the modulation surface 11a.

Subsequently, in step S24, the control unit 13 acquires the second light intensity distribution data (hereinafter referred to as light intensity distribution data $D_C$) through the image sensor 122 in a state in which the above-described phase pattern $P_C$ is displayed (second light intensity distribution acquiring step). In this second light intensity distribution data $D_C$, a converging spot P corresponding to the region B2 is included.

Thereafter, the control unit 13 specifies position coordinates of a converging spot P included in each of two pieces of light intensity distribution data $D_B$ and Dc (step S14), and calculates an amount of angular displacement between the modulation surface 11a and the wavefront sensor 12 based on a relative positional relation between the position coordinates (angle calculating step S15). Also, even in this embodiment, the control unit 13 may adjust an angle around the optical image La of at least one of the modulation surface 11a and the wavefront sensor 12 so that the angular displacement amount calculated in step S15 is reduced (adjusting step S16).

As in this embodiment, the first light intensity distribution data $D_B$ including the converging spot P corresponding to the first region B1 and the second light intensity distribution data Dc including the converging spot P corresponding to the second region B2 may be sequentially acquired, and a relative positional relation between the two converging spots P may be obtained from the light intensity distribution data $D_B$ and $D_C$. Even in this method, the same effects as those of the above-described first embodiment can be obtained.

(Third Embodiment)

In the above-described first and second embodiments, the first phase pattern having linearity in at least one direction is displayed in two regions B1 and B2 and an amount of angular displacement is obtained based on a relative positional relation between converging spots P corresponding to the regions B1 and B2. In the angular displacement detecting method and the adaptive optics system 10 according to an aspect of the present invention, it is possible to obtain the angular displacement amount even in a method to be described below. Also, the configuration of the adaptive optics system 10 is similar to that of the above-described first embodiment except for the operation of the control unit 13.

Figure 24:
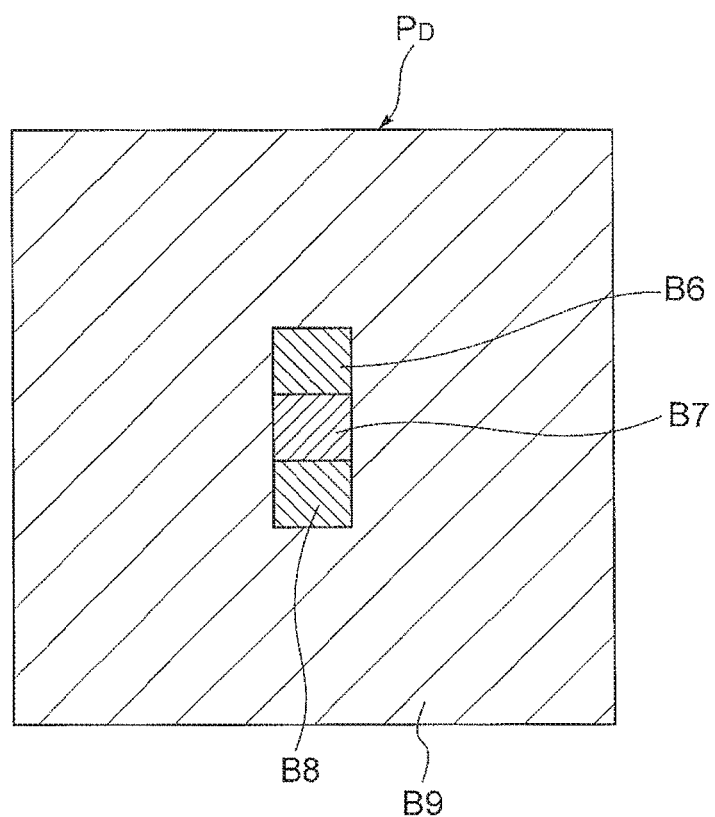
FIG. 24 is a diagram conceptually illustrating a special phase pattern for detecting an amount of angular displacement to be displayed on a modulation surface in a third embodiment.

FIG. 24 is a diagram conceptually illustrating a special phase pattern $P_D$ for detecting an amount of angular displacement to be displayed on the modulation surface 11a in this embodiment. As illustrated in FIG. 24, the phase pattern $P_D$ includes three regions B6 to B8 adjacent to one another arranged in a line in a certain direction. In addition, the phase pattern $P_D$ includes a region B9 surrounding the regions B6 to B8. Also, a length of one side of each of the regions B6 to B8 is similar to those of the regions B1 and B2 of the above-described first and second embodiments.

Figure 25:
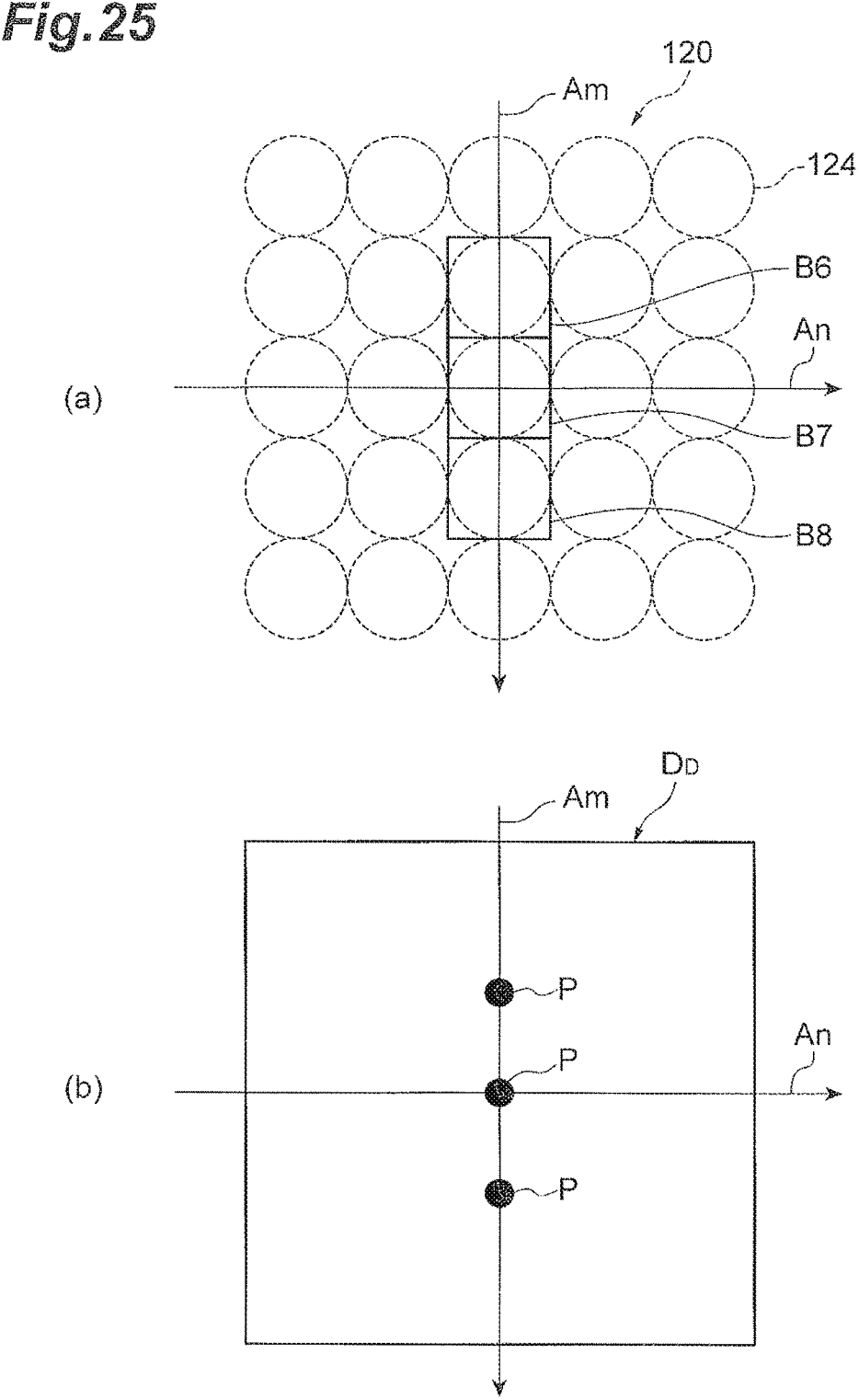
FIG. 25($a$) is a diagram conceptually illustrating a relative relation between each region on the modulation surface and a lens array and illustrates the case in which there is no angular displacement between the modulation surface and the wavefront sensor and the case in which there is no positional displacement between the modulation surface and the wavefront sensor.

FIG. 25(a) is a diagram conceptually illustrating a relative relation between the regions B6 to B8 and the lens array 120 and illustrates the case in which there is no angular displacement between the modulation surface 11a and the wavefront sensor 12 and the case in which there is no positional displacement between the modulation surface 11a and the wavefront sensor 12. FIG. 25(b) is a diagram illustrating light intensity distribution data $D_D$ in the case illustrated in FIG. 25(a). Also, in these drawings, an arrow An denotes a row direction of the modulation surface 11a and an arrow Am denotes a column direction of the modulation surface 11a. As illustrated in FIG. 25(b), converging spots P corresponding to the regions B6 to B8 are clearly shown in the light intensity distribution data $D_D$ when angular displacement and positional displacement between the modulation surface 11a and the wavefront sensor 12 are absent. Also, in the drawing of this embodiment, a clear converging spot P is denoted by a black dot.

Figure 26:
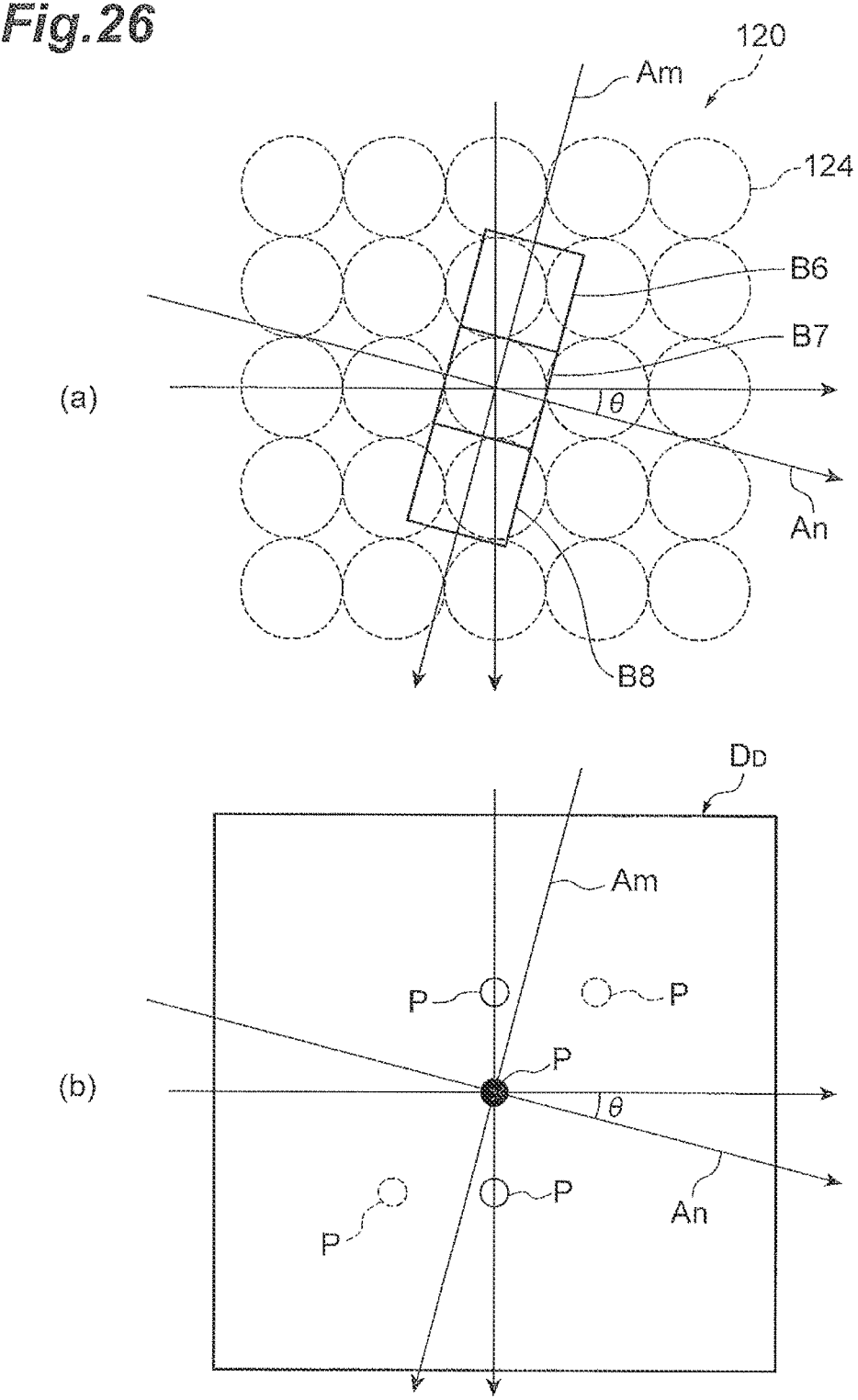
FIG. 26($a$) is a diagram conceptually illustrating a relative relation between each region on the modulation surface and a lens array and illustrates the case in which angular displacement (displacement amount $\theta$) occurs between the modulation surface and the wavefront sensor.

On the other hand, FIG. 26(a) illustrates the case in which angular displacement (displacement amount θ) occurs between the modulation surface 11a and the wavefront sensor 12. In this case, as illustrated in FIG. 26(b), the clarity of the converging spot P corresponding to the region B7 positioned at the rotation center does not change in the light intensity distribution data $D_D$, but the clarity of the converging spots P corresponding to the regions B6 and B8 positioned above and below the region B7 is degraded. In addition, because light is also incident on an adjacent lens 124 in a direction of angular displacement with respect to the lenses 124 corresponding to the regions B6 and B8, a weak converging spot P is formed by these lenses 124. Also, in the drawing of this embodiment, the converging spot P having slightly degraded clarity is denoted by a white dot and the weak converging spot P is denoted by a broken line. Accordingly, it is possible to detect an amount θ of angular displacement between the modulation surface 11a and the wavefront sensor 12 based on the relative positional relation and clarity of these converging spots P.

Figure 27:
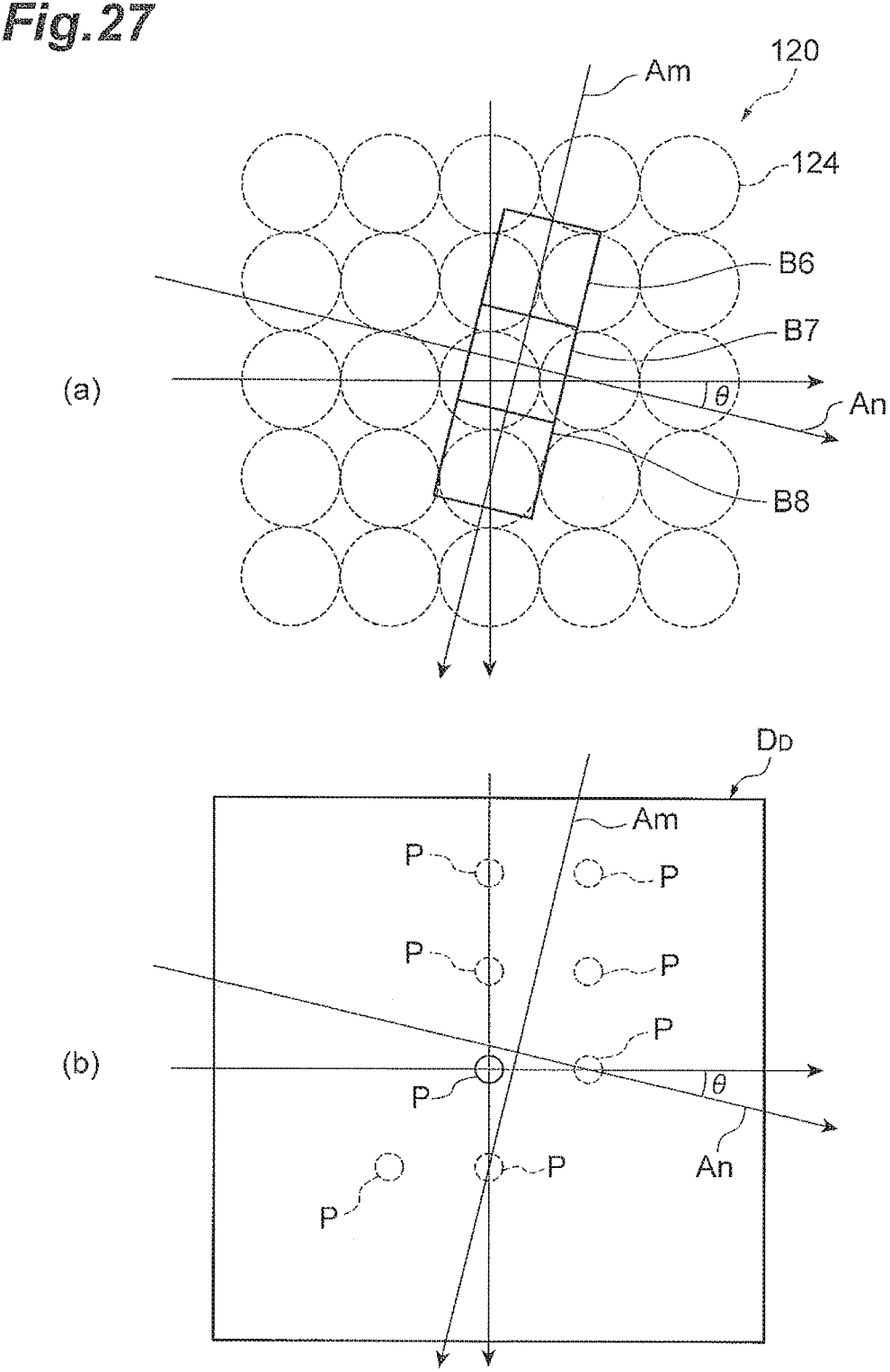
FIG. 27($a$) is a diagram conceptually illustrating a relative relation between each region on the modulation surface and a lens array and illustrates the case in which positional displacement occurs within a surface perpendicular to an optical axis of the optical image in addition to angular displacement (displacement amount $\theta$) between the modulation surface and the wavefront sensor.

Further, FIG. 27(a) illustrates the case in which positional displacement occurs within a plane perpendicular to an optical axis of the optical image La in addition to angular displacement (displacement amount θ) between the modulation surface 11a and the wavefront sensor 12. In this case, as illustrated in FIG. 27(b), the clarity of the converging spot P corresponding to the region B7 is also degraded because the center region B7 is also displaced from a predetermined position. In addition, because light is also incident on the lenses 124 located in a direction of positional displacement of the regions B6 to B8, a plurality of weak converging spots P are formed by these lenses 124. Thereby, the adjustment of relative positions of the modulation surface 11a and the wavefront sensor 12 is performed based on such light intensity distribution data $D_D$ and thereafter it is possible to perform angular adjustment between the modulation surface 11a and the wavefront sensor 12.

Figure 28:
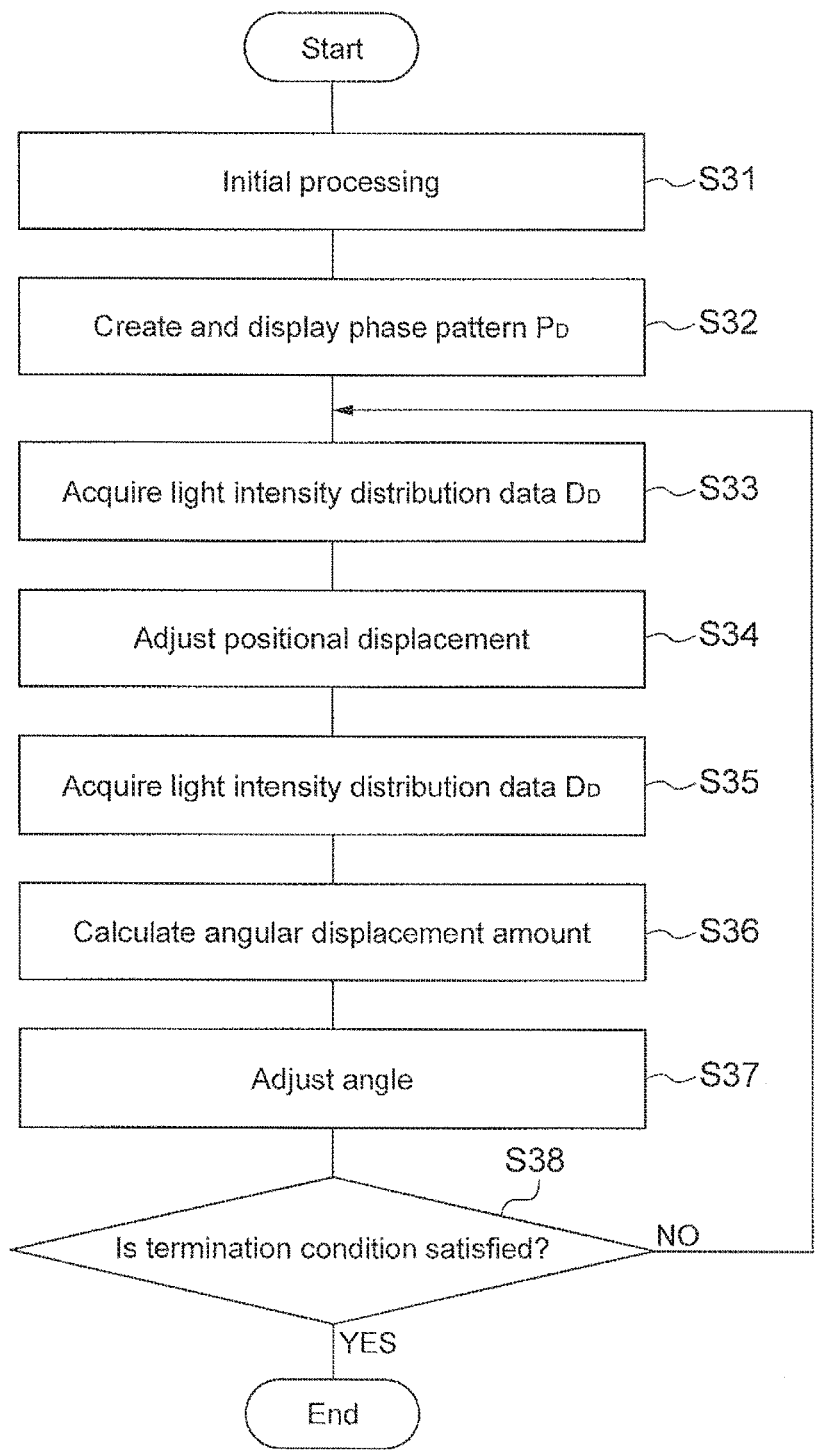
FIG. 28 is a flowchart illustrating an angular displacement detecting method and an operation of a control unit according to a third embodiment.

FIG. 28 is a flowchart illustrating an angular displacement detecting method and an operation of the control unit 13 according to this embodiment. Also, the angular displacement detecting method is stored as a program for the adaptive optics system inside the storage region 13a of the control unit 13 illustrated in FIG. 1 and the control unit 13 executes the angular displacement detecting method by reading the program.

In the adaptive optics system 10, initial processing of the control unit 13 is performed (step S31). Also, details of step S31 are similar to those of step S11 of the above-described first embodiment.

Next, the control unit 13 creates the special phase pattern $P_D$ for detecting the angular displacement amount and displays the created special phase pattern $P_D$ on the modulation surface 11a (step S32). In this step S32, the phase pattern (for example, see FIG. 18) having linearity in at least one direction is displayed in the regions B6 to B8 on the modulation surface 111a corresponding to three lenses 124 arranged in a line among the plurality of lenses 124 of the lens array 120 and the spatially non-linear phase pattern (for example, see FIGS. 12 to 15) is displayed in a region B9 surrounding the regions B6 to B8.

Subsequently, the control unit 13 acquires the light intensity distribution data $D_D$ through the image sensor 122 in a state in which the above-described phase pattern PD is displayed (step S33). Normally, at this time, the light intensity distribution data $D_D$ becomes as in FIG. 27(b) because both the angular displacement and the positional displacement occur between the modulation surface 11a and the wavefront sensor 12. The control unit 13 adjusts the positional displacement between the modulation surface 11a and the wavefront sensor 12 so that the converging spot P corresponding to any one of the regions B6 to B8 (for example, the center region B7) of the light intensity distribution data $D_D$ is clear (step S34). Also, this adjustment of positional displacement is performed by adjusting a relative relation between a mounting position of the wavefront sensor 12 and a mounting position of the spatial light modulator 11. Alternatively, the adjustment of the positional displacement may be performed according to the adjustment of a relative positional relation between position coordinates assumed on the modulation surface 11a when the phase pattern $P_D$ is displayed and the wavefront sensor 12.

Subsequently, the control unit 13 acquires the light intensity distribution data $D_D$ through the image sensor 122 in a state in which the above-described phase pattern $P_D$ is displayed (step S35, light intensity distribution acquiring step). Because the positional displacement between the modulation surface 11a and the wavefront sensor 12 is already adjusted in the above-described step S34, the light intensity distribution data $D_D$ at that time becomes as in FIG. 26(b). The control unit 13 obtains an amount θ of angular displacement between the modulation surface 11a and the wavefront sensor 12 based on a relative relation between position coordinates and clarity of a plurality of converging spots P corresponding to the region B6 and position coordinates and clarity of a plurality of converging spots P corresponding to the region B8 included in the light intensity distribution data $D_D$ (step S36, angle calculating step).

Subsequently, the control unit 13 may adjust an angle around the optical image La of at least one of the modulation surface 11a and the wavefront sensor 12 so that the angular displacement amount θ obtained in step S36 is reduced (step S16, adjusting step). In other words, these angles are adjusted so that the clarity of two converging spots P corresponding to the regions B6 and B8 increases and a weak converging spot P adjacent to the converging spots P corresponding to the regions B6 and B8 is reduced. This adjustment, for example, is performed by adjusting one or both of a mounting angle of the spatial light modulator 11 and a mounting angle of the wavefront sensor 12.

Normally, the positional displacement between the modulation surface 11a and the wavefront sensor 12 is caused by the angular adjustment of step S37. Accordingly, the above-described steps S33 to S37 are iterated until a predetermined termination condition is satisfied (step S38). Alternatively, if position coordinates assumed on the modulation surface 11a are adjusted when the phase pattern $P_D$ is displayed, the above-described steps S32 to S37 are iterated until a predetermined termination condition is satisfied (step S38). If the positional displacement and the angular displacement between the modulation surface 11a and the wavefront sensor 12 are substantially zero (see FIG. 25(b)), the displacement is completed.

Effects obtained by the angular displacement detecting method for the adaptive optics system 10 and the adaptive optics system 10 according to this embodiment described above will be described. In this embodiment, in the light intensity distribution acquiring step S35, the light intensity distribution data $D_D$ is acquired by the image sensor 122 of the wavefront sensor 12 in a state in which the phase pattern having linearity in at least one direction is displayed in the regions B6 to B8 of the spatial light modulator 11 and the spatially non-linear phase pattern is displayed in the region B9 surrounding the regions B6 to B8. In the light intensity distribution data $D_D$, the converging spots P corresponding to the regions B6 to B8 are formed, but the relative positional relation between the converging spots P (particularly, the converging spots P corresponding to the regions B6 to B8) changes according to the amount of angular displacement between the modulation surface 11a and the wavefront sensor 12. Accordingly, it is possible to detect the amount of angular displacement between the modulation surface 11a and the wavefront sensor 12 based on the relative positional relation between the converging spots P corresponding to the regions B6 to B8. In addition, in this embodiment, as in the first embodiment, it is possible to easily and quickly detect the amount of angular displacement according to only an operation of the control unit 13 without requiring the special component or structure for detecting the angular displacement amount.

Also, in this embodiment, in the light intensity distribution acquiring step S35, the light intensity distribution data $D_D$ is acquired in a state in which the first phase pattern having linearity in at least one direction is displayed in the regions B6 to B8. However, it is not necessarily necessary to simultaneously display the first phase patterns to be displayed in the regions B6 to B8. As in the second embodiment, the light intensity distribution data may be acquired while the first phase patterns are sequentially displayed in the regions B6 to B8 and the process of step S36 may be performed based on three pieces of obtained light intensity distribution data.

(Fourth Embodiment)

All the above-described first to third embodiments relate to an amount of angular displacement between the modulation surface 11a and the wavefront sensor 12. In this embodiment, an imaging magnification detecting method for an adaptive optics system 10 and the adaptive optics system 10 including the method and operation common to the first to third embodiments will be described. Also, in this embodiment, the configuration of the adaptive optics system 10 is similar to that of the above-described first embodiment except for the operation of the control unit 13.

Figure 29:
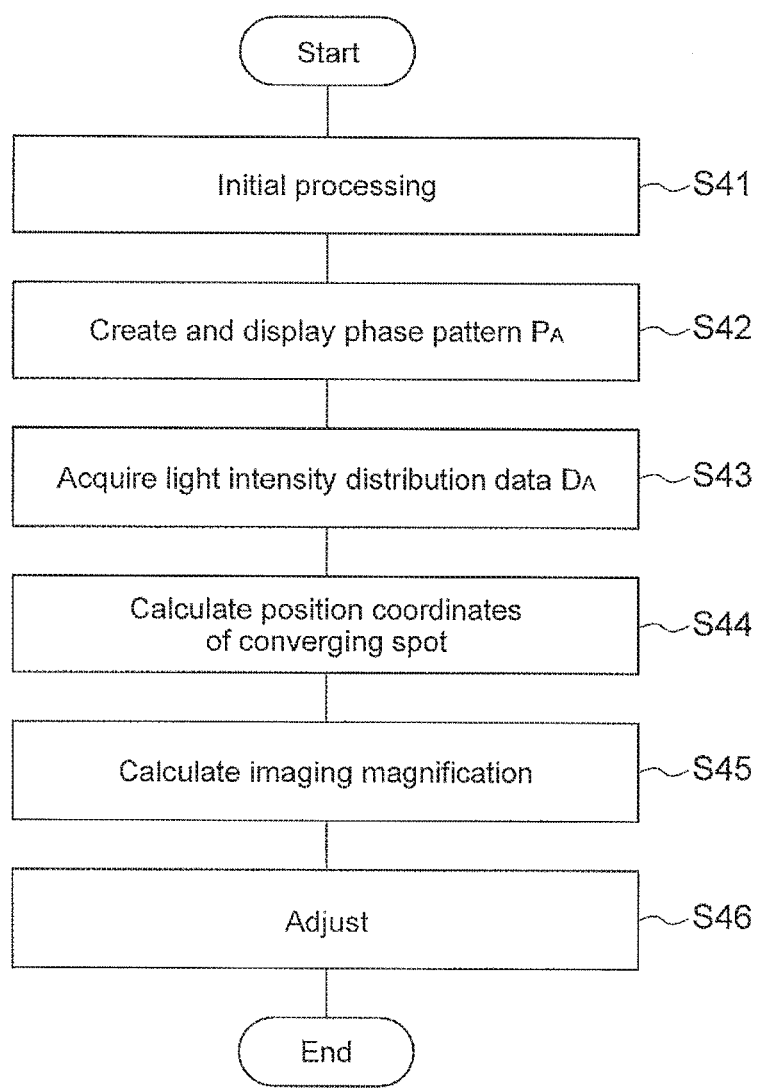
FIG. 29 is a flowchart illustrating an imaging magnification detecting method and an operation of a control unit according to a fourth embodiment.

FIG. 29 is a flowchart illustrating the imaging magnification detecting method and the operation of the control unit 13 according to this embodiment. Also, the imaging magnification detecting method is stored as a program for the adaptive optics system inside the storage region 13a of the control unit 13 illustrated in FIG. 1 and the control unit 13 executes the imaging magnification detecting method by reading the program.

In the adaptive optics system 10, initial processing of the control unit 13 is performed (step S41). Also, details of step S41 are similar to those of step S11 of the above-described first embodiment.

Next, the control unit 13 creates the special phase pattern $P_A$ (see FIG. 8) for detecting imaging magnification and displays the created special phase pattern $P_A$ on the modulation surface 11a (step S42). Also, details of the phase pattern $P_A$ are similar to those of the first embodiment. Thereafter, the control unit 13 acquires the light intensity distribution data $D_A$ through the image sensor 122 in a state in which the above-described phase pattern $P_A$ is displayed (step S43, light intensity distribution acquiring step).

Subsequently, the control unit 13 specifies position coordinates (xp, yp) of each converging spot P by calculating centers of gravity of two converging spots P included in the light intensity distribution data $D_A$ (step S44). Also, a method of calculating the position coordinates (xp, yp) of the converging spot P is similar to step S14 of the above-described first embodiment. Here, the position coordinates of the converging spot P corresponding to the region B1 are designated as ($xp_1$, $yp_1$) and the position coordinates of the converging spot P corresponding to the region B2 are designated as ($xp_2$, $yp_2$).

Subsequently, the control unit 13 calculates imaging magnification M between the modulation surface 11a and the wavefront sensor 12 based on a distance between the position coordinates ($xp_1$, $yp_1$) of the converging spot P corresponding to the region B1 and the position coordinates ($xp_2$, $yp_2$) of the converging spot P corresponding to the region B2 (step S45, magnification calculating step). Here, when the distance between the position coordinates ($xp_1$, $yp_1$) and the position coordinates ($xp_2$, $yp_2$) is designated as H1 and a distance between the center position ($xc_1$, $yc_1$) of the region B1 and the center position ($xc_2$, $yc_2$) of the region B2 is designated as H2, the imaging magnification M is obtained according to a ratio (H1/H2). In other words, the imaging magnification M is obtained according to the following Formula (8).

[Math 8]

$$M = \frac{\sqrt{(xp_2 - xp_1)^2 + (yp_2 - yp_1)^2}}{\sqrt{(xc_2 - xc_1)^2 + (yc_2 - yc_1)^2}} \quad (8)$$

Thereafter, various adjustments are performed based on the imaging magnification M calculated in step S45 (step S46). For example, it is possible to adjust the magnification of a light guide optical system (for example, lenses 15 and 16 illustrated in FIG. 1) arranged between the modulation surface 11a and the wavefront sensor 12 so that the imaging magnification M calculated in step S45 is close to predetermined imaging magnification. This adjustment can be applied when the light guide optical system is constituted of a zoom lens in which the imaging magnification M is variable, etc. Also, because there is a possibility of displacement of a relative position of an optical axis direction between the modulation surface 11a and the wavefront sensor 12 when the imaging magnification M is displaced from the predetermined imaging magnification, for example, it is possible to adjust an optical distance between the modulation surface 11a and the wavefront sensor 12 so that the imaging magnification M calculated in step S45 is close to the predetermined imaging magnification. In addition, for example, it is also possible to adjust a size of a region in which a phase pattern for compensating for wavefront distortion is displayed on the modulation surface 11a based on the imaging magnification M calculated in step S45.

Effects obtained by the imaging magnification detecting method for the adaptive optics system 10 and the adaptive optics system 10 according to this embodiment described above will be described. In this embodiment, in the light intensity distribution acquiring step S43, the light intensity distribution data DA is acquired by the image sensor 122 of the wavefront sensor 12 in a state in which the phase pattern having linearity in at least one direction is displayed in the regions B1 and B2 of the spatial light modulator 11 and the spatially non-linear phase pattern is displayed in the region B3 surrounding the regions B1 and B2. In the light intensity distribution data $D_A$, the converging spots P corresponding to the regions B1 and B2 are formed, but the distance between the converging spots P changes according to the imaging magnification M between the modulation surface 11a and the wavefront sensor 12. Accordingly, it is possible to detect the imaging magnification M between the modulation surface 11a and the wavefront sensor 12 based on the distance between the converging spots P corresponding to the regions B1 and B2. In addition, in this embodiment, it is possible to easily and quickly detect the imaging magnification M according to only an operation of the control unit 13 without requiring the special component or structure for detecting the imaging magnification M.

(Fifth Embodiment)

In the above-described fourth embodiment, the light intensity distribution data $D_A$ is acquired in a state in which the first phase pattern having linearity in at least one direction is displayed in the regions B1 and B2 in the light intensity distribution acquiring step S43. However, it is not necessarily necessary to simultaneously display the first phase pattern to be displayed in the regions B1 and B2 as in the second embodiment in the imaging magnification detecting method either.

Figure 30:
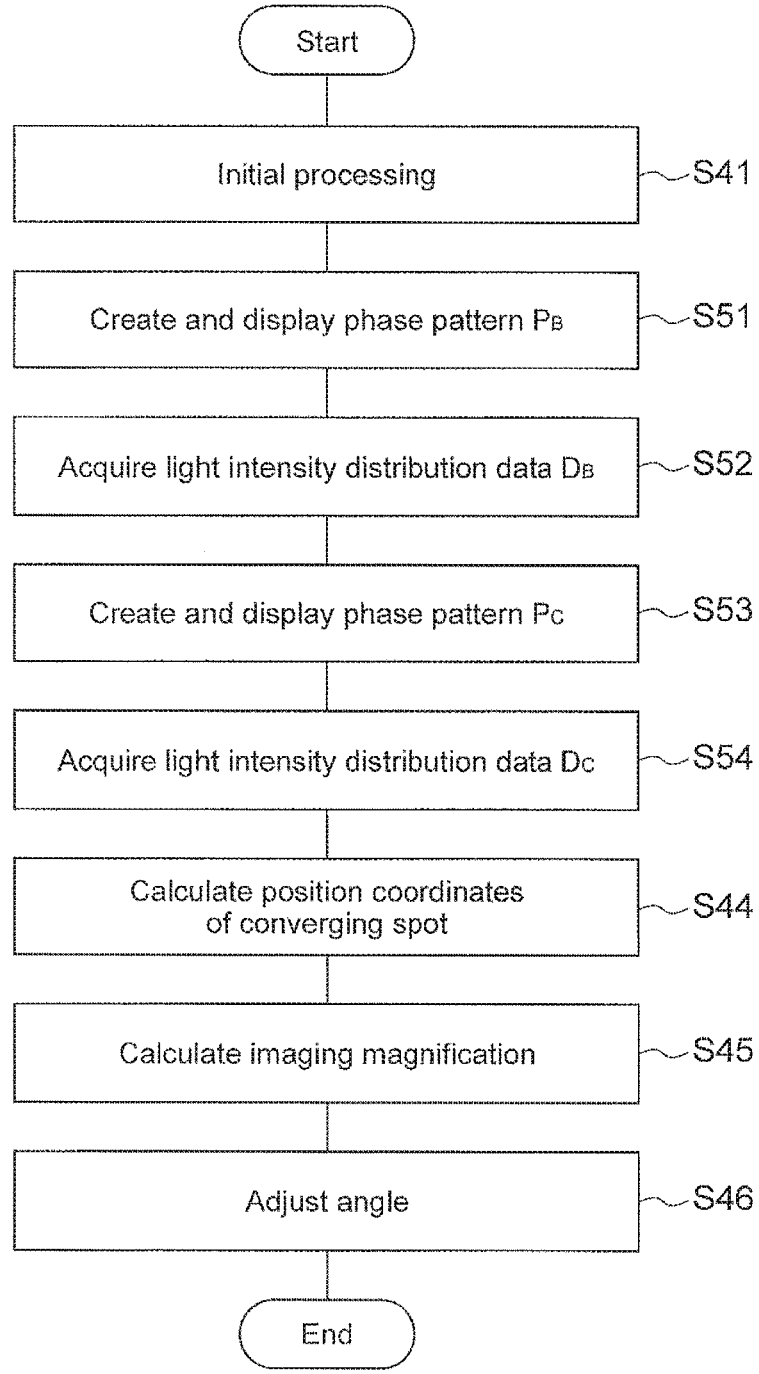
FIG. 30 is a flowchart illustrating an imaging magnification detecting method and an operation of a control unit according to a fifth embodiment.

FIG. 30 is a flowchart illustrating the imaging magnification detecting method and the operation of the control unit 13 according to the fifth embodiment. A difference between this embodiment and the above-described first embodiment is that steps S51 to S54 are provided instead of steps S42 and S43 illustrated in FIG. 29. Also, because the other steps are similar to those of the above-described fourth embodiment, detailed description thereof will be omitted.

In step S51, the control unit 13 creates a special phase pattern $P_B$ (see FIG. 22) for detecting the imaging magnification and displays the created special phase pattern $P_B$ on the modulation surface 11a. Details of the phase pattern $P_B$ are similar to those of the second embodiment. Thereafter, in step S52, the control unit 13 acquires the first light intensity distribution data $D_B$ through the image sensor 122 in a state in which the above-described phase pattern $P_B$ is displayed (first light intensity distribution acquiring step). The converging spot P corresponding to the region B1 is included in the first light intensity distribution data $D_B$.

Subsequently, in step S53, the control unit 13 creates a special phase pattern $P_C$ (see FIG. 23) for detecting the imaging magnification and displays the created special phase pattern $P_C$ on the modulation surface 11a. Also, details of the phase pattern $P_C$ are similar to those of the second embodiment. Thereafter, in step S54, the control unit 13 acquires second light intensity distribution data Dc through the image sensor 122 in a state in which the above-described phase pattern $P_C$ is displayed (second light intensity distribution acquiring step). The converging spot P corresponding to the region B2 is included in the second light intensity distribution data $D_C$.

Thereafter, the control unit 13 specifies position coordinates of converging spots P included in two pieces of light intensity distribution data $D_B$ and $D_C$ obtained in steps S51 to S54 (step S44) and calculates imaging magnification M between the modulation surface 11a and the wavefront sensor 12 based on a distance between the position coordinates (magnification calculating step S45). Thereafter, various adjustments are performed in step S46.

As in this embodiment, the first light intensity distribution data $D_B$ including the converging spot P corresponding to the first region B1 and the second light intensity distribution data Dc including the converging spot P corresponding to the second region B2 may be sequentially acquired and a distance between the two converging spots P may be obtained from the light intensity distribution data $D_B$ and $D_C$. Even in this method, similar effects to the above-described fourth embodiment can be obtained.

FIRST MODIFIED EXAMPLE

Figure 32:
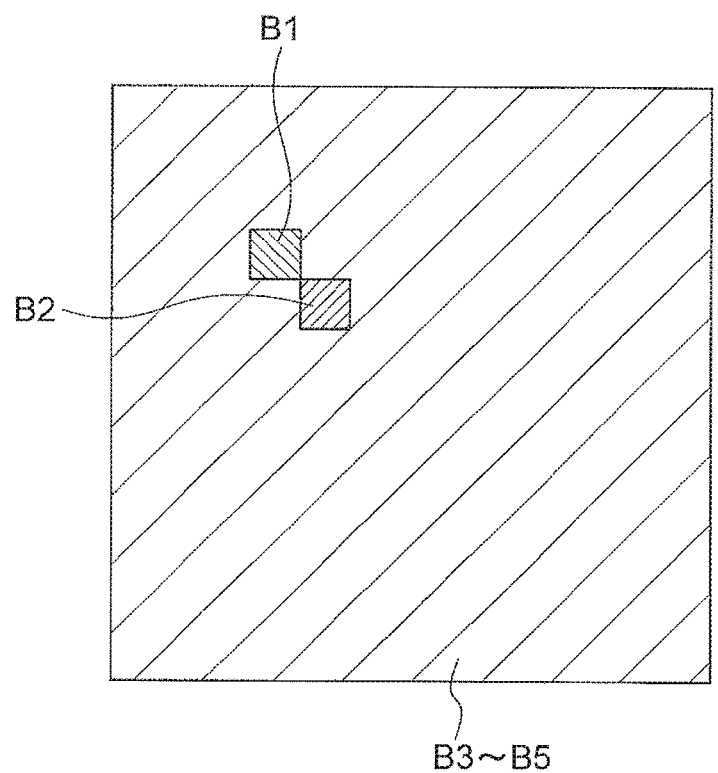
FIG. 32 is a diagram illustrating an example of an arrangement of first and second regions.

Although the case in which the first region B1 and the second region B2 are regions separated from each other is shown in the above-described embodiments except the third embodiment, for example, the first region B1 and the second region B2 may be regions adjacent to each other in a row or column direction as illustrated in FIGS. 31(a) and 31(b). Alternatively, for example, as illustrated in FIG. 32, the first region B1 and the second region B2 may be regions adjacent to each other in a diagonal direction. Even when the regions B1 and B2 are arranged as described above, it is possible to obtain similar effects to the above-described embodiments. However, when the regions B1 and B2 are separated from each other, corresponding converging spots P are unlikely to overlap each other. Accordingly, the regions B1 and B2 may be separated from each other according to a shape of a first phase pattern having linearity.

SECOND MODIFIED EXAMPLE

In the above-described embodiment, the first phase pattern having the linearity in at least one direction is displayed in the regions B1 and B2 (or the regions B6 to B8) and the spatially non-linear second phase pattern is displayed in the regions B3 to B5 (or the region B9). However, even when the first phase pattern having the linearity in at least one direction is displayed in the regions B3 to B5 (or the region B9) and the spatially non-linear second phase pattern is displayed in the regions B1 and B2 (or the regions B6 to B8), it is possible to obtain similar effects to the above-described embodiments. In this case, the above-described Formula (3) is rewritten as follows.

[Math 9]

$$P_A(n, m) = \begin{cases} rand\,() & (n, m) \subset ROI \\ a & (n, m) \not\subset ROI \end{cases} \quad (9)$$

In this modified example, converging spots P corresponding to the regions B1 and B2 (or the regions B6 to B8) become unclear and converging spots P corresponding to the regions B3 to B5 (or the region B9) around the regions B1 and B2 (or the regions B6 to B8) become clear. In this case, it is possible to calculate the amount of angular displacement (or the imaging magnification M) between the modulation surface 11a and the wavefront sensor 12 based on a relative relation (or distance) between position coordinates of the converging spot P formed around the region B1 (or the region B6) and position coordinates of the converging spot p formed around the region B2 (or the region B8).

According to this modified example, as in the above-described embodiment, it is possible to easily detect the amount of angular displacement about the optical axis (or the imaging magnification M) between the modulation surface 11a and the wavefront sensor 12.

Because the phase pattern having linearity can be displayed in all regions other than the regions B1 and B2 (or the regions B6 to B8), it is possible to detect the amount of angular displacement about the optical axis (or the imaging magnification M) in parallel during adaptive optical execution by designating the phase pattern as a phase pattern for compensating for wavefront distortion.

THIRD MODIFIED EXAMPLE

In the above-described embodiments, a substantially uniform distribution expressed by a constant a has been shown as an example of a first phase pattern having linearity in at least one direction displayed in the regions B1 and B2 or B6 to B8 (the regions B3 to B5 or B9 in the second modified example). However, the first phase pattern may be a phase distribution inclined in at least one direction (changed linearly). Also, a phase pattern $P_A$ including the above-described phase pattern is expressed by the following Formula (10).

[Math 10]

$$P_A(n, m) = \begin{cases} a + b(n - n_0) + c(m - m_0) & (n, m) \subset ROI \\ rand\,() & (n, m) \not\subset ROI \end{cases} \quad (10)$$

Here, $n_0$ and $m_0$ denote center pixels of the regions B1 and B2 (ROI) and a, b, and c are constants.

Figure 33:
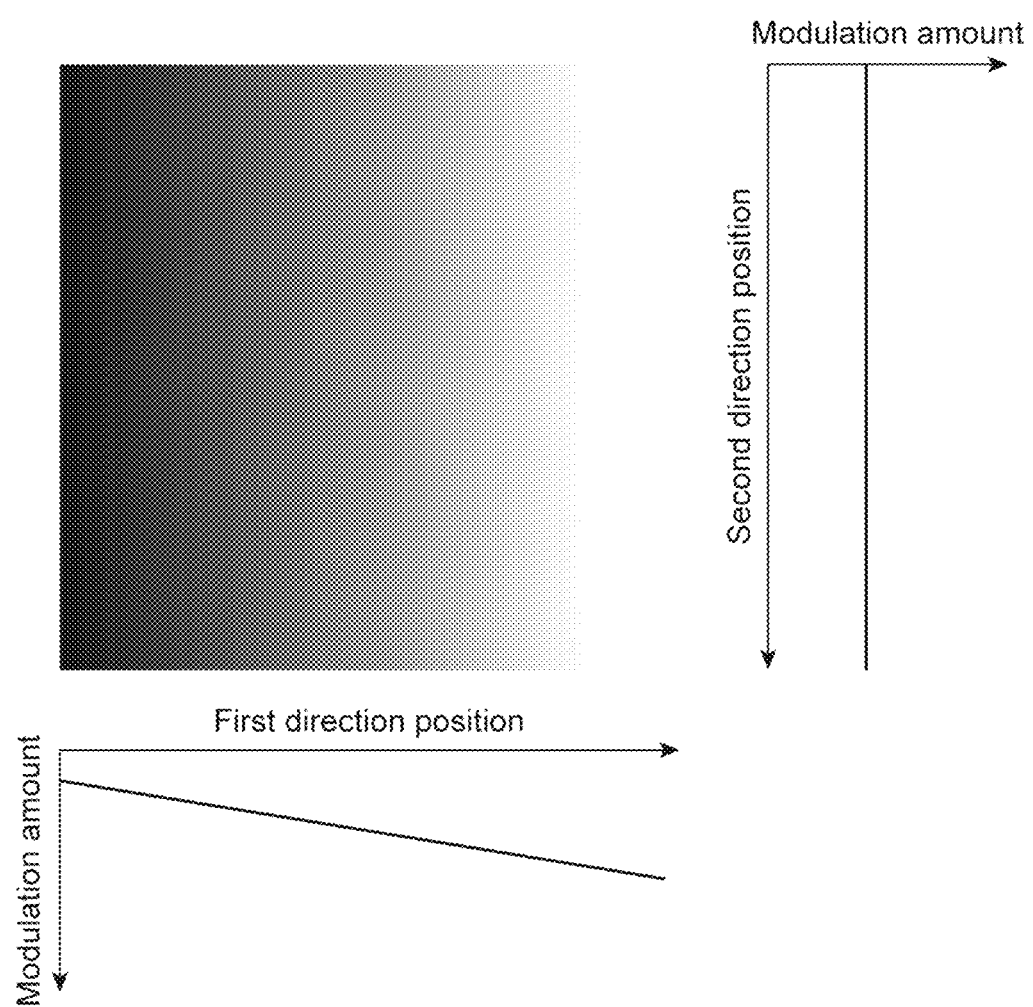
FIG. 33 is a diagram illustrating a phase distribution in which phase values are inclined in a first direction (for example, a row direction) and phase values are substantially uniform in a second direction (for example, a column direction) intersecting the first direction.
Figure 34:
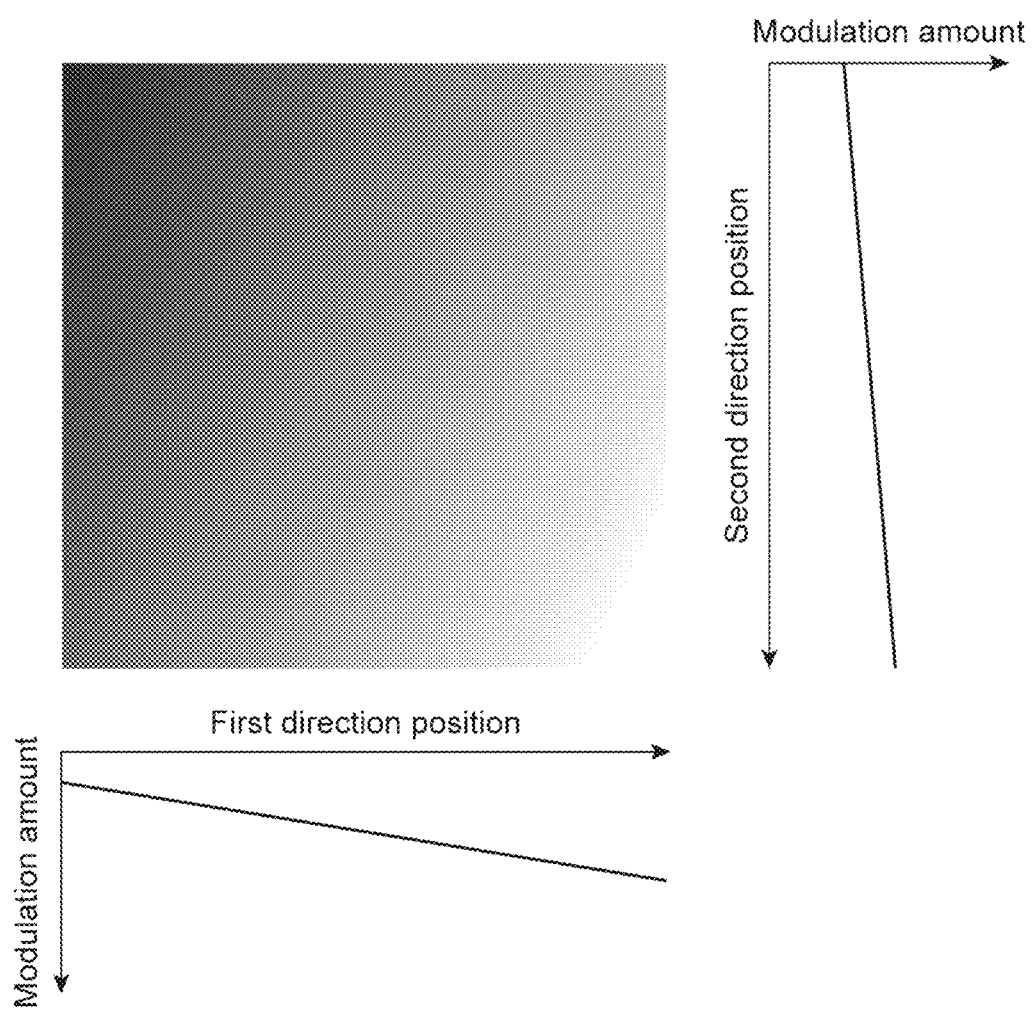
FIG. 34 is a diagram illustrating a phase distribution in which phase values are inclined in both the first direction (for example, the row direction) and the second direction (for example, the column direction).

FIG. 33 illustrates a phase distribution in which phase values are inclined in a first direction (for example, a row direction) and phase values are substantially uniform in a second direction (for example, a column direction) intersecting the first direction. This is a phase distribution in ROI of the case in which b≠0 and c=0 in the above-described Formula (10). Also, FIG. 34 illustrates a phase distribution in which phase values are inclined in both the first direction (for example, the row direction) and the second direction (for example, the column direction). This is a phase distribution in ROI of the case in which b≠0 and c≠0 in the above-described Formula (10). Also, a graph of a phase modulation amount in one position of each of row and column directions is also illustrated in FIGS. 33 and 34.

Because the wavefront of the optical image La of the relevant part is flat when these phase patterns are displayed in the regions B1 and B2 or B6 to B8, the clear converging spot P is formed by the lens 124. Accordingly, as in the above-described embodiments and modified examples, it is possible to detect the angular displacement amount or the imaging magnification M based on the relative positional relation or the distance between the converging spots P.

However, in this modified example, the center of gravity position of the converging spot P is displaced by a slope of the first phase pattern. Accordingly, when the angular displacement amount or the imaging magnification M is detected, it is possible to perform similar calculation to the above-described embodiments in consideration of the displacement of a center of gravity position. Also, a displacement amount of the center of gravity position of the converging spot P is uniquely defined based on a configuration parameter of the wavefront sensor 12 and the coefficients b and c. In addition, because it is possible to obtain the original center of gravity position by subtracting the above-described displacement amount from the center of gravity position of the converging spot P, it is possible to detect the angular displacement amount or the imaging magnification M according to a similar procedure to the above-described embodiments.

FOURTH MODIFIED EXAMPLE

Figure 35:
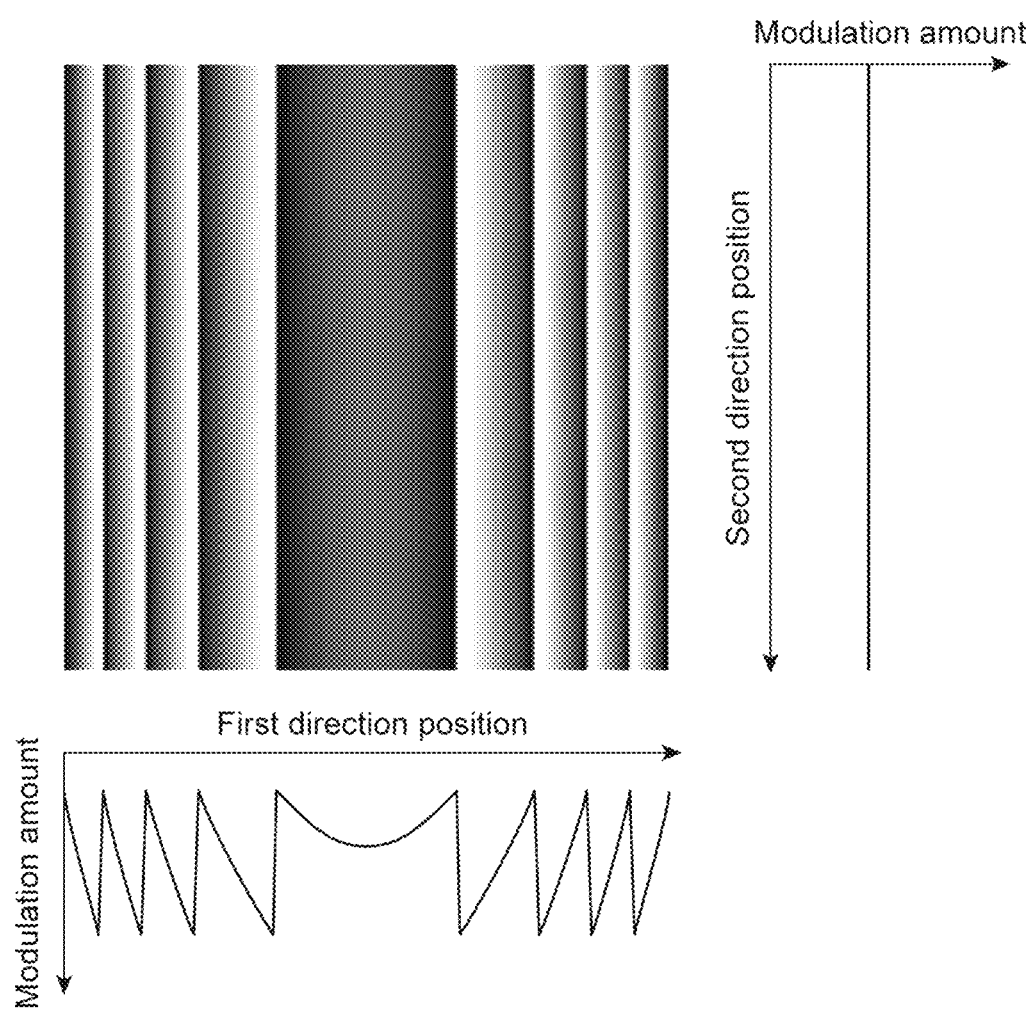
FIG. 35 is a diagram illustrating a phase distribution having a cylindrical lens effect in the first direction and in which phase values are substantially uniform in the second direction as an example of a phase pattern having linearity in at least one direction.

The first phase pattern displayed in the regions B1 and B2 or B6 to B8 (the regions B3 to B5 or the region B9 in the second modified example) may be a phase distribution having a quadratic function in the first direction and in which phase values are substantially uniform in the second direction (that is, a phase distribution having the cylindrical lens effect in the first direction) as illustrated in FIG. 35. Also, this phase pattern $P_A$ including such a phase distribution is expressed by the following Formula (11).

[Math 11]

$$P_A(n, m) = \begin{cases} a_1 + b_1(n - n_1)^2 & (n, m) \subset ROI(n_1, m_1) \\ a_2 + b_2(n - n_2)^2 & (n, m) \subset ROI(n_2, m_2) \\ rand\,() & (n, m) \not\subset (ROI(n_1, m_1) \cup ROI(n_2, m_2)) \end{cases} \quad (11)$$

In the above-described Formula (11), $n_1$ and $m_1$ denote center pixels of the region B1 (ROI($n_1$, $m_1$)), $n_2$ and $m_2$ denote center pixels of the region B2 (ROI($n_2$, $m_2$)) and $a_1$, $b_1$, $a_2$, and $b_2$ denote constants.

When the phase pattern illustrated in FIG. 35 is displayed on the modulation surface 11a, a converging spot P extending in the first direction and converging in the second direction is formed in the wavefront sensor 12. Thereby, it is possible to obtain a position of the converging spot P to be formed in the second direction. Subsequently, when the phase pattern $P_A$ of the phase distribution (that is, a phase distribution having the cylindrical lens effect in the second direction) in which the first and second directions are interchanged is displayed on the modulation surface 11a, the position of the converging spot P in the first direction is obtained. Accordingly, it is possible to detect the angular displacement amount or the imaging magnification as in the above-described embodiments and first to third modified examples using the phase pattern having linearity in at least one direction as in FIG. 35. Alternatively, the phase pattern $P_A$ including a phase distribution having the cylindrical lens effect can be created by the following Formula (12).

[Math 12]

$$P_A(n, m) = \begin{cases} a_1 + b_1(n - n_1)^2 & (n, m) \subset ROI(n_1, m_1) \\ a_2 + b_2(m - m_2)^2 & (n, m) \subset ROI(n_2, m_2) \\ rand\,() & (n, m) \not\subset (ROI(n_1, m_1) \cup ROI(n_2, m_2)) \end{cases} \quad (12)$$

The phase pattern $P_A$ expressed by the following Formula (12) is different from the phase pattern expressed by Formula (11), has a quadratic function in the first direction in the region B1, and has a quadratic function in the second direction in the region B2. When phase pattern $P_A$ expressed by the following Formula (12) is displayed on the modulation surface 11a, the position of the second direction is obtained based on the converging spot P corresponding to the region B1, that is, the converging spot P extending in the first direction and converging in the second direction. In addition, the position of the first direction is obtained based on the converging spot P corresponding to the region B2, that is, the converging spot P extending in the second direction and converging in the first direction. Subsequently, when the phase pattern $P_A$ including phase distributions obtained by interchanging the phase distributions of the regions B1 and B2 (that is, a phase distribution having a quadratic function in the second direction in the region B1 and a phase distribution having a quadratic function in the first direction in the region B2) is displayed on the modulation surface 11a, the position of the first direction is obtained based on the converging spot P extending in the second direction corresponding to the region B1 and the position of the second direction is obtained based on the converging spot P extending in the first direction corresponding to the region B2. It is possible to detect the angular displacement amount or the imaging magnification as in the above-described embodiments and modified examples using positions of converging spots P corresponding to the regions B1 and B2.

FIFTH MODIFIED EXAMPLE

Figure 36:
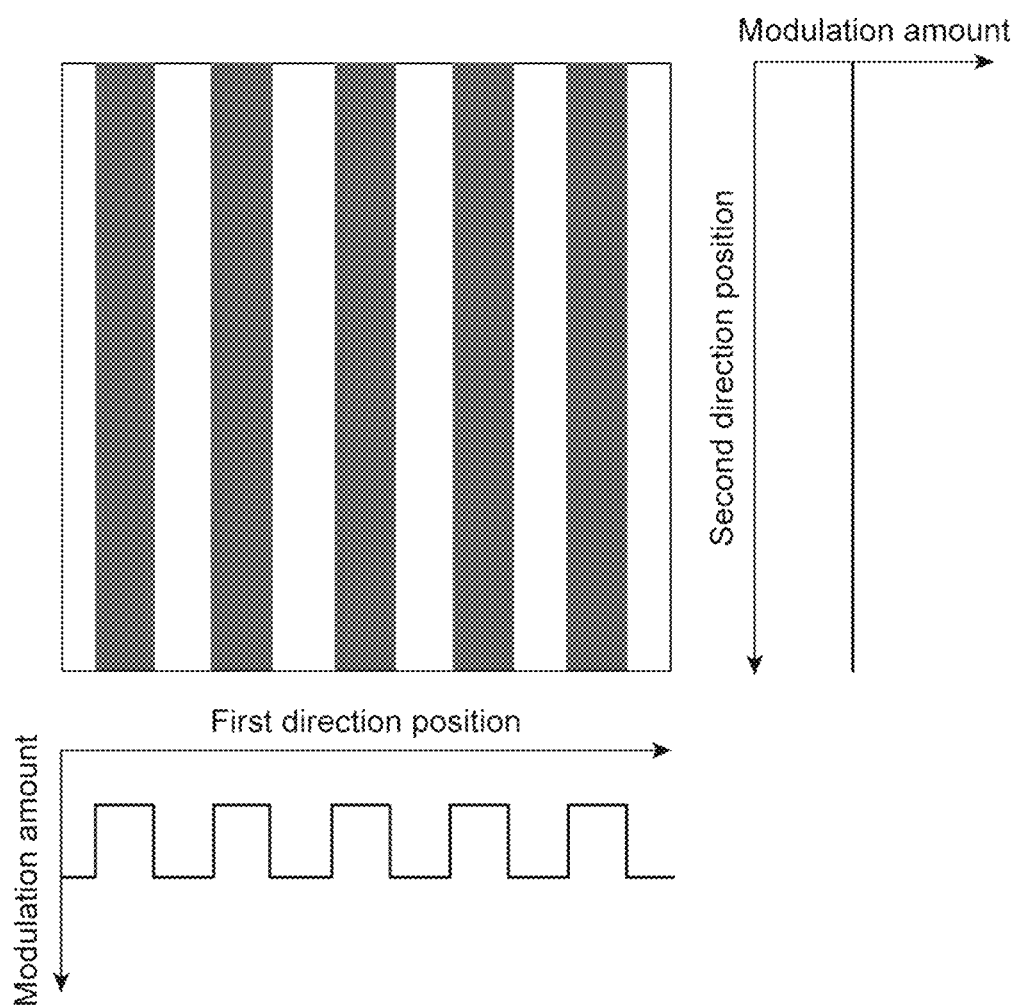
FIG. 36 is a diagram illustrating a phase distribution constituting a diffraction grating in the first direction and in which phase values are substantially uniform in the second direction as an example of a phase pattern having linearity in at least one direction.

First phase patterns displayed in regions B1 and B2 or B6 to B8 (the regions B3 to B5 or the region B9 in the second modified example) may have a phase distribution constituting a diffraction grating in the first direction and in which phase values are substantially uniform in the second direction as illustrated in FIG. 36. When the phase pattern illustrated in FIG. 36 is displayed on the modulation surface 11a, a plurality of converging spots P separated in the first direction and converging in the second direction are formed in the wavefront sensor 12. Accordingly, the position of the converging spot P in the second direction is obtained. Subsequently, the position of the converging spot P in the first direction is obtained using phase patterns including phase distributions in which the direction of the diffraction grating rotates 90 degrees in the regions B1 and B2. It is possible to detect the angular displacement amount or the imaging magnification as in the above-described embodiments and modified examples using positions of converging spots P corresponding to the regions B1 and B2.

SIXTH MODIFIED EXAMPLE

First phase patterns displayed in regions B1 and B2 or B6 to B8 (the regions B3 to B5 or the region B9 in the second modified example) may include a composite pattern in which phase distributions shown in the first embodiment and the third to fifth modified examples are mutually superimposed. FIG. 37 is a diagram illustrating an example of the composite pattern obtained by such superimposition. The phase pattern illustrated in FIG. 37(a) is the phase pattern illustrated in FIG. 35 and the phase pattern illustrated in FIG. 37(b) is the phase pattern obtained by rotating the phase pattern illustrated in FIG. 33 90 degrees. The phase pattern illustrated in FIG. 37(c) is a composite pattern in which the phase patterns are superimposed and is a phase pattern of a phase distribution having a quadratic function in the first direction and a linear function in the second direction. When the composite pattern illustrated in FIG. 37(c) is displayed on the modulation surface 11a, the converging spot P extending in the first direction and converging in the second direction is formed in the wavefront sensor 12. Accordingly, the position of the converging spot P to be formed in the second direction is obtained. Also, the displacement amount is included at the obtained position of the second direction according to an inclined phase distribution as in FIG. 37(b). It is possible to obtain the original center of gravity position of the second direction by subtracting the displacement amount. Subsequently, it is possible to obtain the center of gravity position of the first direction by displaying a phase pattern obtained by rotating the phase pattern illustrated in FIG. 37(c) 90 degrees. It is possible to detect the angular displacement amount or the imaging magnification as in the above-described embodiments and modified examples using positions of converging spots P corresponding to the regions B1 and B2.

SEVENTH MODIFIED EXAMPLE

In the above-described embodiments and modified examples, examples of the random distribution (FIG. 12) and the defocus distribution (FIG. 13) are shown as an example of the spatially non-linear second phase pattern displayed in the regions B3 to B5 (the region B9 in the second modified example). The second phase pattern is not limited thereto, but it is only necessary for the second phase pattern to have a phase distribution so that a clear converging spot P is not formed. As this phase distribution, for example, there is a Fresnel zone plate (FZP) type phase pattern. The FZP type phase pattern has a function of converging or diverging an incident optical image La having a substantially uniform phase value. Accordingly, when the optical image La converged or diverged by the FZP type phase pattern is incident on the lens 124, the position of the optical axis direction of the converging spot P is displaced from a focal plane of the lens 124 (that is, the surface of the image sensor 122). Thus, a blurred point image is formed in the surface of the image sensor 122.

The phase pattern $P_A$ including this FZP type phase pattern is expressed by the following Formula (13).

[Math 13]

$$P_A(n, m) = \begin{cases} a_1 + b_1(n - n_0) + c_1(m - m_0) & (n, m) \subset ROI \\ a_2 + b_2((n - n_k)^2 + (m - m_k)^2) & (n, m) \not\subset ROI \end{cases} \quad (13)$$

Here, $a_2$ denotes a constant and $b_2$ denotes a sufficiently large constant. $(n_k, m_k)$ denotes center pixels of the regions B3 to B5. Also, when $b_2$ is sufficiently large, it is possible to sufficiently separate the converging spot P formed by the lens 124 from the focal plane of the lens 124 (the surface of the image sensor 122).

EIGHTH MODIFIED EXAMPLE

Figure 38:
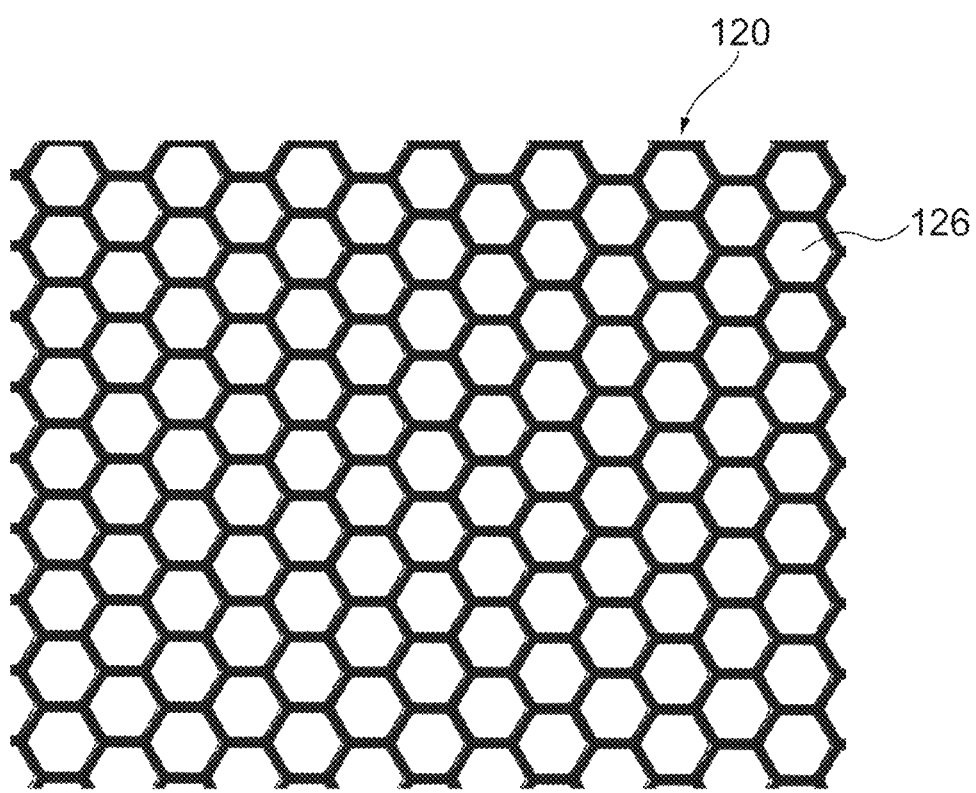
FIG. 38 is a diagram illustrating a modified example of a lens array.

In the above-described embodiments and modified examples, an example of a form in which the plurality of lenses 124 are arranged as the lens array 120 of the wavefront sensor 12 in the two-dimensional lattice shape as illustrated in FIG. 3 is shown. However, the lens array of the wavefront sensor 12 is not limited to such a form. For example, as illustrated in FIG. 38, the lens array 120 may have a honeycomb structure in which a plurality of regular hexagonal lenses 128 are arranged without gaps. Also, in this case, the regions B1 and B2 or the regions B6 to B8 may be set in a hexagonal shape.

In addition, a form in which a plurality of regular hexagonal pixels are arranged without gaps may be used as the spatial light modulator. In addition, the spatial light modulator is described as an example in the above-described embodiments, but a spatial light modulator using a material having an electro-optic effect other than liquid crystal, a spatial light modulator in which a pixel is formed of a micro-mirror, a variable mirror for deforming a film mirror using an actuator, or the like may be used.

Figure 39:
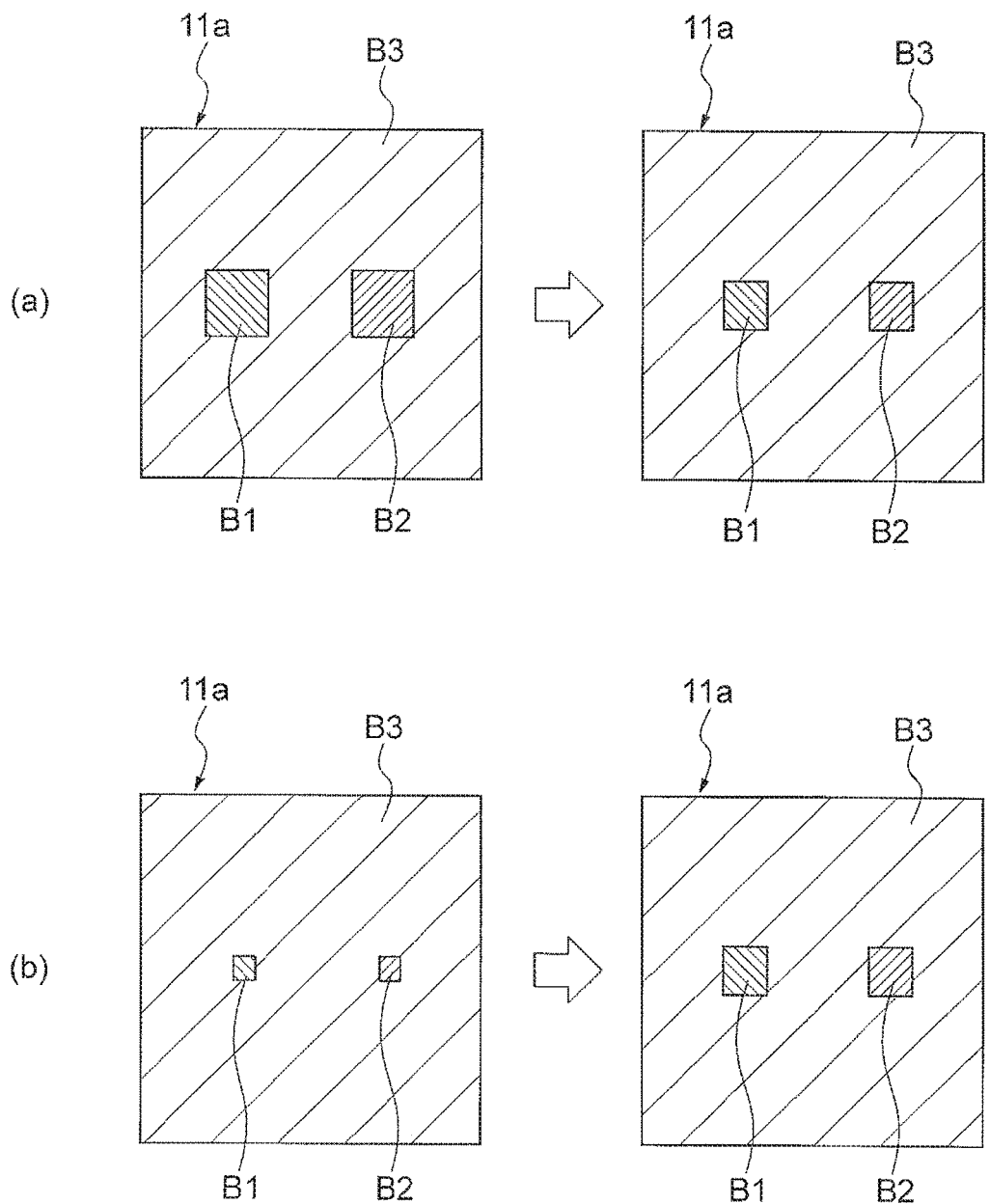
FIG. 39 is a diagram illustrating an example of the case in which sizes of first and second regions are configured to be variable.

An angular displacement detecting method for an adaptive optics system, an imaging magnification detecting method for an adaptive optics system, and an adaptive optics system according to an aspect of the present invention are not limited to the above-described embodiments, and other various modifications are possible. For example, sizes of the regions B1 and B2 or the regions B6 to B8 are preset and the angular displacement amount, etc. are detected in the above-described embodiments and modified examples, but the sizes of the regions B1 and B2 or the regions B6 to B8 may be variable. FIG. 39 is a diagram illustrating an example of the case in which sizes of first and second regions B1 and B2 are configured to be variable. In the example illustrated in FIG. 39($a$), the sizes of the regions B1 and B2 are set to be relatively large and reduced to an appropriate size (for example, a size corresponding to the diameter of the lens 124) based on the obtained light intensity distribution data. In addition, in the example illustrated in FIG. 39($b$), the sizes of the regions B1 and B2 are set to be relatively small and enlarged to an appropriate size (for example, a size corresponding to the diameter of the lens 124) based on the obtained light intensity distribution data. As described above, the sizes of the regions B1 and B2 (or the regions B6 to B8) are set to be variable, so that it is possible to set the regions B1 and B2 (or the regions B6 to B8) having an appropriate size and further precisely detect the angular displacement amount or the imaging magnification. In addition, the phase patterns to be displayed in the regions B1 and B2 need not necessarily be the same. For example, the phase pattern having the cylindrical effect as in FIG. 35 may be displayed in the region B1 and the phase pattern having the structure of the diffraction grating as in FIG. 36 may be displayed in the region. B2.

In addition, although the case in which the adaptive optics system includes one spatial light modulator is shown in the above-described embodiments and modified examples, the adaptive optics system may include a plurality of spatial light modulators coupled optically. When the plurality of spatial light modulators are coupled in series, it is possible to detect the angular displacement amount or the imaging magnification between one spatial light modulator and the wavefront sensor by causing one spatial light modulator to display the phase pattern $P_A$ (or $P_D$) and causing the other spatial light modulator to display, for example, the substantially uniform phase pattern. In addition, when the plurality of spatial light modulators are coupled in parallel, it is possible to detect the angular displacement amount or the imaging magnification between one spatial light modulator and the wavefront sensor by causing one spatial light modulator to display the phase pattern $P_A$ (or $P_D$) and causing the other spatial light modulator to display, for example, the substantially uniform phase pattern or by shielding an optical image before or after incidence on the other spatial light modulator. Such an operation is performed by each of the plurality of spatial light modulators, so that it is possible to detect amounts of angular displacement and imaging magnifications between all spatial light modulators and the wavefront sensor.

INDUSTRIAL APPLICABILITY

According to an angular displacement detecting method for an adaptive optics system and an adaptive optics system according to an aspect of the present invention, it is possible to easily detect angular displacement about an optical axis between a modulation surface of a spatial light modulator and a wavefront sensor. Also, according to an imaging magnification detecting method for an adaptive optics system and an adaptive optics system according to an aspect of the present invention, it is possible to easily detect imaging magnification between a modulation surface of a spatial light modulator and a wavefront sensor.

REFERENCE SIGNS LIST

10 Adaptive optics system
11 Spatial light modulator
11$a$ Modulation surface
12 Wavefront sensor
13 Control unit
14 Beam splitter
15, 16 Relay lens
17 Control circuit unit
18 Optical detection element
120 Lens array
122 Image sensor
122$a$ Light receiving surface
122$b$ Pixel
124 Lens
B1 First region
B2 Second region
D1, D2, $D_A$ to $D_D$ Light intensity distribution data
La Optical image
P Converging spot
$P_A$ to $P_D$ Phase pattern

The invention claimed is:

1. An angular displacement detecting method for an adaptive optics system, which includes a spatial light modulator configured to spatially modulate a phase of an optical image incident on a modulation surface and a wavefront sensor including a lens array having a plurality of two-dimensionally arranged lenses and an optical detection element for detecting a light intensity distribution including converging spots formed by the lens array and configured to receive the optical image after the modulation from the spatial light modulator and which compensates for wavefront distortion by controlling a phase pattern displayed in the spatial light modulator based on a wavefront shape of the optical image obtained from the light intensity distribution, wherein an amount of angular displacement between the modulation surface and the wavefront sensor is calculated, the angular displacement detecting method comprising:
- a light intensity distribution acquiring step of acquiring the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions; and
- an angle calculating step of obtaining the amount of angular displacement between the modulation surface and the wavefront sensor based on a relative positional relation between the converging spot corresponding to the first region and the converging spot corresponding to the second region included in the light intensity distribution obtained in the light intensity distribution acquiring step.

2. The angular displacement detecting method for the adaptive optics system according to claim 1, further comprising:
- an adjusting step of adjusting an angle around the optical image of at least one of the modulation surface and the wavefront sensor so that the amount of angular displacement calculated in the angle calculating step is reduced.

3. The angular displacement detecting method for the adaptive optics system according to claim 1, wherein the first and second regions are regions adjacent to each other.

4. The angular displacement detecting method for the adaptive optics system according to claim 1, wherein the first and second regions are regions separated from each other.

5. An angular displacement detecting method for an adaptive optics system, which includes a spatial light modulator configured to spatially modulate a phase of an optical image incident on a modulation surface and a wavefront sensor including a lens array having a plurality of two-dimensionally arranged lenses and an optical detection element for detecting a light intensity distribution including converging spots formed by the lens array and configured to receive the optical image after the modulation from the spatial light modulator and which compensates for wavefront distortion by controlling a phase pattern displayed in the spatial light modulator based on a wavefront shape of the optical image obtained from the light intensity distribution, wherein an amount of angular displacement between the modulation surface and the wavefront sensor is calculated, the angular displacement detecting method comprising:
- a first light intensity distribution acquiring step of acquiring a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region;
- a second light intensity distribution acquiring step of acquiring a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region; and
- an angle calculating step of obtaining the amount of angular displacement between the modulation surface and the wavefront sensor based on a relative positional relation between the converging spot corresponding to the first region included in the first light intensity distribution and the converging spot corresponding to the second region included in the second light intensity distribution.

6. An imaging magnification detecting method for an adaptive optics system, which includes a spatial light modulator configured to spatially modulate a phase of an optical image incident on a modulation surface and a wavefront sensor including a lens array having a plurality of two-dimensionally arranged lenses and an optical detection element for detecting a light intensity distribution including converging spots formed by the lens array and configured to receive the optical image after the modulation from the spatial light modulator and which compensates for wavefront distortion by controlling a phase pattern displayed in the spatial light modulator based on a wavefront shape of the optical image obtained from the light intensity distribution, wherein imaging magnification between the modulation surface and the wavefront sensor is detected, the imaging magnification detecting method comprising:
- a light intensity distribution acquiring step of acquiring the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions; and
- a magnification calculating step of obtaining the imaging magnification between the modulation surface and the wavefront sensor based on a distance between the converging spot corresponding to the first region and the converging spot corresponding to the second region included in the light intensity distribution obtained in the light intensity distribution acquiring step.

7. The imaging magnification detecting method for the adaptive optics system according to claim 6, further comprising:
- an adjusting step of adjusting the magnification of a light guide optical system arranged between the modulation surface and the wavefront sensor so that the imaging magnification calculated in the magnification calculating step is close to predetermined imaging magnification.

8. The imaging magnification detecting method for the adaptive optics system according to claim 6, further comprising:
- an adjusting step of adjusting an optical distance between the modulation surface and the wavefront sensor so that the imaging magnification calculated in the magnification calculating step is close to predetermined imaging magnification.

9. The imaging magnification detecting method for the adaptive optics system according to claim 6, further comprising:

an adjusting step of adjusting a size of a region on the modulation surface in which the phase pattern for compensating for the wavefront distortion is displayed based on the imaging magnification calculated in the magnification calculating step.

10. The imaging magnification detecting method for the adaptive optics system according to claim 6, wherein the first and second regions are regions adjacent to each other.

11. The imaging magnification detecting method for the adaptive optics system according to claim 6, wherein the first and second regions are regions separated from each other.

12. An imaging magnification detecting method for an adaptive optics system, which includes a spatial light modulator configured to spatially modulate a phase of an optical image incident on a modulation surface and a wavefront sensor including a lens array having a plurality of two-dimensionally arranged lenses and an optical detection element for detecting a light intensity distribution including converging spots formed by the lens array and configured to receive the optical image after the modulation from the spatial light modulator and which compensates for wavefront distortion by controlling a phase pattern displayed in the spatial light modulator based on a wavefront shape of the optical image obtained from the light intensity distribution, wherein imaging magnification between the modulation surface and the wavefront sensor is detected, the imaging magnification detecting method comprising:

a first light intensity distribution acquiring step of acquiring a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region;

a second light intensity distribution acquiring step of acquiring a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region; and a magnification calculating step of obtaining the imaging magnification between the modulation surface and the wavefront sensor based on a distance between the converging spot corresponding to the first region included in the first light intensity distribution and the converging spot corresponding to the second region included in the second light intensity distribution.

13. An adaptive optics system comprising:

a spatial light modulator configured to spatially modulate a phase of an optical image incident on a modulation surface;

a wavefront sensor including a lens array having a plurality of two-dimensionally arranged lenses and an optical detection element for detecting a light intensity distribution including converging spots formed by the lens array and configured to receive the optical image after the modulation from the spatial light modulator; and a control unit configured to compensate for wavefront distortion by controlling a phase pattern displayed in the spatial light modulator based on a wavefront shape of the optical image obtained from the light intensity distribution, wherein the control unit acquires the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions and obtains the amount of angular displacement between the modulation surface and the wavefront sensor based on a relative positional relation between the converging spot corresponding to the first region and the converging spot corresponding to the second region included in the light intensity distribution.

14. An adaptive optics system comprising:

a spatial light modulator configured to spatially modulate a phase of an optical image incident on a modulation surface;

a wavefront sensor including a lens array having a plurality of two-dimensionally arranged lenses and an optical detection element for detecting a light intensity distribution including converging spots formed by the lens array and configured to receive the optical image after the modulation from the spatial light modulator; and a control unit configured to compensate for wavefront distortion by controlling a phase pattern displayed in the spatial light modulator based on a wavefront shape of the optical image obtained from the light intensity distribution, wherein the control unit acquires a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region, acquires a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region, and obtains the amount of angular displacement between the modulation surface and the wavefront sensor based on a relative positional relation between the converging spot corresponding to the first region included in the first light intensity distribution and the converging spot corresponding to the second region included in the second light intensity distribution.

15. An adaptive optics system comprising:

a spatial light modulator configured to spatially modulate a phase of an optical image incident on a modulation surface;

a wavefront sensor including a lens array having a plurality of two-dimensionally arranged lenses and an optical detection element for detecting a light intensity distribution including converging spots formed by the lens array and configured to receive the optical image after the modulation from the spatial light modulator; and a control unit configured to compensate for wavefront distortion by controlling a phase pattern displayed in the spatial light modulator based on a wavefront shape of the optical image obtained from the light intensity distribution, wherein the control unit acquires the light intensity distribution through the optical detection element in a state in which one of a phase pattern having linearity in at least one direction and a spatially non-linear phase pattern is displayed in first and second regions on the modulation surface corresponding to one of the plurality of lenses or two or more lenses adjacent to each other and the other is displayed in a region surrounding the first and second regions, and obtains the imaging magnification between the modulation surface and the wavefront sensor based on a distance between the converging spot corresponding to the first region and the converging spot corresponding to the second region included in the light intensity distribution.

16. An adaptive optics system comprising:

a spatial light modulator configured to spatially modulate a phase of an optical image incident on a modulation surface;

a wavefront sensor including a lens array having a plurality of two-dimensionally arranged lenses and an optical detection element for detecting a light intensity distribution including converging spots formed by the lens array and configured to receive the optical image after the modulation from the spatial light modulator; and a control unit configured to compensate for wavefront distortion by controlling a phase pattern displayed in the spatial light modulator based on a wavefront shape of the optical image obtained from the light intensity distribution, wherein the control unit acquires a first light intensity distribution through the optical detection element in a state in which one of a phase pattern having linearity in at least one direction and a spatially non-linear phase pattern is displayed in a first region on the modulation surface corresponding to one of the plurality of lenses or two or more lenses adjacent to each other and the other is displayed in a region surrounding the first region, acquires a second light intensity distribution through the optical detection element in a state in which one of a phase pattern having linearity in at least one direction and a spatially non-linear phase pattern is displayed in a second region which is a region separate from the first region on the modulation surface corresponding to one of the plurality of lenses or two or more lenses adjacent to each other and the other is displayed in a region surrounding the second region, and obtains the imaging magnification between the modulation surface and the wavefront sensor based on a distance between the converging spot corresponding to the first region included in the first light intensity distribution and the converging spot corresponding to the second region included in the second light intensity distribution.

* * * * *